(12) United States Patent
Dunne et al.

(10) Patent No.: US 8,216,975 B2
(45) Date of Patent: Jul. 10, 2012

(54) METHOD OF LABELLING SOYA VARIETIES

(75) Inventors: Cheryl Dunne, Vero Beach, FL (US);
Ulrich Johannes Haas, Stein (CH);
Michael Johnson, Greensboro, NC (US); Willy Rüegg, Basel (CH)

(73) Assignee: Syngenta Crop Protection Inc, Greensboro, NC (US)

( * ) Notice: Subject to any disclaimer, the term of this patent is extended or adjusted under 35 U.S.C. 154(b) by 772 days.

(21) Appl. No.: 11/116,562

(22) Filed: Apr. 28, 2005

(65) Prior Publication Data
US 2005/0246800 A1 Nov. 3, 2005

Related U.S. Application Data

(60) Provisional application No. 60/566,251, filed on Apr. 29, 2004.

(51) Int. Cl.
*A01N 25/00* (2006.01)
(52) U.S. Cl. .................................................. 504/116.1
(58) Field of Classification Search ................ 504/116.1
See application file for complete search history.

(56) References Cited

FOREIGN PATENT DOCUMENTS
WO   WO 00/15615   *   3/2000

OTHER PUBLICATIONS

Young et al. Weed Technology, 2003, 17:651-654.*
Dyck et al. Ecological Application, 1993, 3: 92-122.*
Institute of Food Research (IFR Communications): soya.*
Dyck et al. (Ecological Application, 1993, 3: 92-122).*
The report of IFR Communications: Soya by Institute of Food Research (published on May 8, 2003 and retreated via Internet Archive http://web.archive.org/web/*/http://www.ifr.ac.uk/public/FoodInfoShet/soya.html).*
Young et al. (Weed Technology: 2003, vol. 17, p. 651-654).*
Young et al. (Weed Technology, 2003, 17: 651-654).*

* cited by examiner

*Primary Examiner* — Johann Richter
*Assistant Examiner* — Mei-Ping Chui
(74) *Attorney, Agent, or Firm* — James Cueva

(57) ABSTRACT

The present invention is directed to a method which enables the user to select a suitable soya variety as a subsequent crop to maize when weed control in that maize crop has been carried out using HPPD inhibitor herbicides in a manner that "carry-over" damage to the soya crop is thereby avoided. The method includes the step of first selecting a "reference soya" that exhibits a visually determinable phytotoxicity with respect to the HPPD inhibitor herbicide used to carry out weed control on the maize crop. Next, the phytotoxicity of various soya varieties is determined in relation to the reference soya variety in the form of a factor. This factor can be expressed, for example, in letters, numbers, symbols, colors or other visual or acoustic signals or in words. These soya varieties are then labeled with the factor and can be made accessible to the user. For example, the factor can be indicated on or inside the product packaging or in an accompanying leaflet.

3 Claims, No Drawings

METHOD OF LABELLING SOYA VARIETIES

This application claims the benefit of U.S. Provisional Application No. 60/566,251, filed Apr. 29, 2004, now abandoned.

The present invention relates to a method of labeling soya varieties (*Glycine max*) as to their suitability as a subsequent crop to maize.

In the cultivation of crop plants, especially on a commercial scale, correct crop rotation is crucially important for yield stability (the achievement of high yields of good quality over a long period) and for the economic success of an agronomic business. For example, across large areas of the main maize-growing regions of the USA (the "central corn belt"), soya is grown as the subsequent crop to maize in over 75% of cases. Selective weed control in maize crops is increasingly being carried out using HPPD inhibitor herbicides. Although that class of herbicides has excellent suitability for that purpose, it can result in agronomically unacceptable phytotoxic damage to the crop plants in subsequent crops, especially in subsequent soya crops, because certain soya varieties are sensitive to even very small residues of such HPPD inhibitor herbicides ("carry-over" damage).

When a user, having used HPPD inhibitor herbicides in a maize crop, chooses soya as the subsequent crop, he currently has no satisfactory way of determining simply and with sufficient exactness from the several thousand commercially available varieties the suitability of a certain soya variety for growing as a subsequent crop to maize and thus of avoiding agronomically unacceptable phytotoxic damage to the soya crop. It is therefore the aim of the present invention to provide a method which enables the user to select, in a simple manner, a suitable soya variety as a subsequent crop to maize when weed control in that maize crop has been carried out using HPPD inhibitor herbicides, in order that "carry-over" damage to the soya crop is thereby avoided. That aim is achieved by the provision of the method according to the invention.

The method according to the invention for the labeling of soya varieties as to their suitability as a subsequent crop to maize when weed control in that maize crop has been carried out using HPPD inhibitor herbicides is as follows:

a) in a first step, a reference soya variety is selected which, when grown as a subsequent crop to maize wherein weed control has been carried out using HPPD inhibitor herbicides, exhibits a visually determinable phytotoxicity with respect to those HPPD inhibitor herbicides;

b) in a second step, the phytotoxicity of soya varieties when grown as a subsequent crop to maize wherein weed control has been carried out using HPPD inhibitor herbicides is determined in relation to that reference soya variety in the form of a factor; and c) in a third step, said soya varieties are labeled with said factor.

Method Step a):

In the context of the present invention, the term "visually determinable phytotoxicity" is to be understood as being phytotoxic damage that is clearly visible. That value is preferably from 5 to 60% phytotoxicity, more especially from 5 to 20% phytotoxicity.

Suitable reference soya varieties within the scope of the present invention are those varieties which can be tested in agronomic, biological, biochemical, molecular-biological, physical or chemical test procedures in the field, in the greenhouse, in climatic cabins, in climatic cabinets, in the form of whole plants, cell cultures, organelle cultures, in soil, in nutrient solutions, in hydrocultures, in gelled nutrient media or in some other suitable form and exhibit measurable damage caused by residues of HPPD inhibitors in the soil. Particularly suitable are varieties that have comparable sensitivity or are more sensitive to those HPPD inhibitors than the variety NK S40-R9. Varieties that are only slightly (e.g. less than a factor of 2 with respect to the $ED_{20}$ of variety NK S40-R9; see Table C) more tolerant than variety NK S40-R9 in a measurable form are likewise designated sensitive.

Preferred sensitive reference soya varieties are varieties selected from NK S40-R9, Pioneer 94B01, NK S46-W8, Mustang M-222RR, AGI 7370 RR, Pioneer 9492, Pioneer 93B67, Pioneer 90B51, S. Grow SG948R and Pioneer 94B54.

Method Step b):

The factor in Method step b) can be expressed in letters, numbers, symbols, colours or other visual or acoustic signals or in words. For example, the factors can be indicated by the letters A, B, C, D and E. The reference soya variety is given a fixed reference value, for example "C". The phytotoxicity of the soya varieties is indicated with reference to that factor. For example, a soya variety having two times higher resistance to the HPPD inhibitor herbicides can be given the factor "D", while a soya variety having four times higher resistance to the HPPD inhibitor herbicides can be given the factor "E". A soya variety having the factor "B" would be less suitable as a subsequent crop to maize when weed control in that maize crop had been carried out using HPPD inhibitor herbicides, while a soya variety having the factor "A" would be unsuitable. Alternatively, for example, numbers from 1 to 10 could be used, the fixed point of the reference soya variety being chosen as desired, or terms such as "low suitability", "suitability", "good suitability" and "very good suitability" or "non-tolerant" and "tolerant" could be used. It is also possible to give factors that relate to the application of specific HPPD inhibitor herbicides, for example the commercially available herbicides mesotrione, isoxaflutole or sulcotrione. Factors indicating the phytotoxicity of the soya crops with respect to specific HPPD inhibitor herbicides are more exact, which further increases the reliability of use.

Method Step c):

The labeling of a soya variety with a factor can be made accessible to the user in various ways. The factor can be indicated on or inside the product packaging or in an accompanying leaflet or it can be given in lists or tabular works in documents (publications, posters, leaflets) or on electronic or optical data supports or on the Internet, television or video, or made available as part of interactive programs or business methods for improving methods and yields in agriculture. The factor can also be publicised by direct oral communication (conversation, lecture, radio, telephone).

Biological Test Method for the Selection of Suitable Sensitive Reference Soybean Varieties in the Field:

a) Compound No. 2.13 according to Table 2 below was applied pre- or post-emergence to maize in three repetitions in a field in the vicinity of Ames, Iowa, USA, under practical conditions at a suitable time (pre-emergence April-May; post-emergence May-June) in a field trial using concentrations of 100, 200 and 400 g a.i./ha. Application of fertilizer, pest control and other cultivation measures were carried out in accordance with the standards customary in agriculture. Because not all weeds were controlled by the test herbicides, the test plots were kept weed-free over the entire vegetation period by the application of non-soil-active herbicides.

b) The plots were harvested and labeled in the autumn. At the customary time in early summer (April/May) of the following year, the soybeans to be tested were sown in the labeled plots from the previous year and the condition of the plants on reaching the different physiological growth stages was evaluated (see Table 1).

c) The evaluation was carried out in % general phytotoxicity, which records any effects such as growth inhibition, bleaching, chlorosis, scorching or thinning. 0-4% phytotoxicity is acceptable, >4% is not acceptable under practical field conditions.

Tables A and B: Phytotoxicity of the soya varieties S40R-9 and S24-K4 as a subsequent crop to maize in which weed control has been carried out using the herbicide of formula 2.13. The herbicide was applied in an amount of 400 g/ha; in Table B an oil adjuvant (Agridex) was additionally used in an amount of 1.25% by volume.

3. 3-4 Weeks after sowing, the condition of the plants is evaluated visually. Symptoms of damage to the plants, such as chlorosis, bleaching and growth inhibition ('stunting'), are assessed and compared with an untreated soya plant of the same variety.

4. Calculation: The repetitions are combined and a linear regression analysis is carried out with non-transformed data. $ED_{20}$ values (=effective dose at which damage is 20% in comparison with the untreated control) are calculated from the regression curve for each variety. The soybeans are grouped according to whether they are "sensitive" or "tolerant" by comparing the $ED_{20}$ values

TABLE A

| Soya evaluation date | Soya sowing date | Days after sowing | Soya variety | Days after HPPD herbicide application | % Phytotoxicity (mean value) | Development stage of the crop plant on evaluation (minimum/maximum) |
|---|---|---|---|---|---|---|
| 18.06.03 | 20.05.03 | 29 | NK S40-R9 | 404 | 6.67 | BBCH12/BBCH13 |
| 18.06.03 | 20.05.03 | 29 | NK-S24-K4 | 404 | 0 | BBCH12/BBCH13 |
| 01.07.03 | 20.05.03 | 42 | NK S40-R9 | 417 | 13 | BBCH14/BBCH14 |
| 01.07.03 | 20.05.03 | 42 | NK-S24-K4 | 417 | 0 | BBCH14/BBCH14 |
| 15.07.03 | 20.05.03 | 56 | NK S40-R9 | 431 | 14.33 | BBCH16/BBCH17 |
| 15.07.03 | 20.05.03 | 56 | NK-S24-K4 | 431 | 0 | BBCH16/BBCH17 |

TABLE B

| Soya evaluation date | Soya sowing date | Days after sowing | Soya variety | Days after HPPD herbicide application | % Phytotoxicity (mean value) | Development stage of the crop plant on evaluation (minimum/maximum) |
|---|---|---|---|---|---|---|
| 18.06.03 | 20.05.03 | 29 | NK S40-R9 | 404 | 36.67 | BBCH12/BBCH13 |
| 18.06.03 | 20.05.03 | 29 | NK-S24-K4 | 404 | 5.67 | BBCH12/BBCH13 |
| 01.07.03 | 20.05.03 | 42 | NK S40-R9 | 417 | 49.33 | BBCH14/BBCH14 |
| 01.07.03 | 20.05.03 | 42 | NK-S24-K4 | 417 | 3.33 | BBCH14/BBCH14 |
| 15.07.03 | 20.05.03 | 56 | NK S40-R9 | 431 | 56.67 | BBCH16/BBCH17 |
| 15.07.03 | 20.05.03 | 56 | NK-S24-K4 | 431 | 1.67 | BBCH16/BBCH17 |

It can be seen from the above results that the variety S40R-9 reacts very sensitively to the residues of the HPPD inhibitors and exhibits a "carry-over" effect, while the variety S24-K4 is largely resistant.

Test Method for the Selection of Suitable Soybean Varieties: Categorisation of the Soybean Varieties According to Their Sensitivity to HPPD Herbicide Residues and Comparison with Sensitive and Non-Sensitive Soybean Varieties:

1. A non-sterilised soil is treated with the HPPD inhibitor being tested. The HPPD inhibitor being tested is applied in concentrations of 0, 20, 40 and 80 ppb and incorporated homogeneously into the soil. The soil so treated is then introduced into pots (2⅝ inch×2⅝ inch×3½ inch) and lightly firmed.

2. Sowing: The soybean varieties being tested are sown in the pots treated as described above as follows: 3 seed grains are used per pot, the seeds being pressed lightly into the soil (under the surface of the soil) and covered over with soil. In each test, varieties having known sensitivity are also tested as reference. These are the soybean varieties NK S40-R9 and Pioneer P94B01. Shortly after germination, the plants are thinned out to two plants per pot. The plants receive an optimum supply of water and nutrients and are kept in a greenhouse at 20-24° C., with 16 hours exposure to light per day.

of the test varieties with those of the standard varieties, that is to say by determining a factor with respect to the reference variety.

Results relating to the selection and confirmation of suitable sensitive reference soybean varieties in the field. Ranking of soybean sensitivity and comparison with sensitive and non-sensitive soybean varieties.

The following Table C shows factors for the selection of suitable soybean varieties. As HPPD inhibitor herbicide there was used the herbicide of formula 2.13 of Table 2 indicated below.

TABLE C

Factor with respect to reference variety NK S40-R9, based on ED20 values:

| Soya variety | Factor |
|---|---|
| NK S46-W8 | 0.5 |
| Pioneer 94B01 | 0.8 |
| Mustang M-222RR | 0.8 |
| AGI 7370 RR | 1.0 |
| Pioneer 9492 | 1.0 |
| NK S40-R9 | 1.0 |
| Pioneer 93B67 | 1.1 |
| Pioneer 90B51 | 1.1 |
| S. Grow SG948RR | 1.2 |

TABLE C-continued

Factor with respect to reference variety NK S40-R9, based on ED20 values:

| Soya variety | Factor |
|---|---|
| Pioneer 94B54 | 1.6 |
| Pioneer 91B91 | 3.0 |
| Kruger 279 RR | 3.4 |
| NK S24-K4 | 3.6 |
| Garst 2677 RR | 4.1 |
| Dekalb DKB36-51 | 4.2 |
| Pioneer P92B38 | 4.3 |
| Kruger 323 RR | 4.3 |
| MFA RT 3660N | 4.3 |
| D King 4868RR | 4.4 |
| Asgrow AG1401 RR | 4.5 |
| Beck's 336NRR | 4.5 |
| S34-A9 STS | 8.0 |
| Asgrow AG3902 | 4.7 |
| Agripro 2547 RR/N | 4.7 |
| Asgrow AG2302 | 4.7 |
| Pioneer 91B33 | 4.9 |
| Beck's 366NRR | 4.9 |
| Asgrow 2705 | 5.0 |
| S21-H7 STS | 5.03 |
| NK S35-A6 | 5.3 |
| Dekalb DK32-51 | 5.3 |
| Agripro 2502 RR | 5.3 |
| Asgrow 1602 | 5.4 |
| Agway APK256 RR | 5.6 |
| Dekalb DKB23-51 | 5.8 |
| Gld H H3505RR | 5.8 |
| Asgrow 2105 | 6.5 |
| Asgrow AG4403 | 8.5 |
| Agway APK 190 | 12.2 |

The following Table D shows factors for the selection of suitable soybean varieties. As HPPD inhibitor herbicide there was used the herbicide of formula 2.04 of Table 2 indicated below.

TABLE D

Factor with respect to reference variety NK S40-R9, based on ED20 values:

| Soya variety | Factor |
|---|---|
| S40-R9 | 1.0 |
| S21-H7 STS | 3.45 |
| S34-A9 STS | 4.56 |

The following Table E shows factors for the selection of suitable soybean varieties. As HPPD inhibitor herbicide there was used the herbicide of formula 2.10 of Table 2 indicated below.

TABLE E

Factor with respect to reference variety NK S40-R9, based on ED20 values:

| Soya variety | Factor |
|---|---|
| S40-R9 | 1.0 |
| S21-H7 STS | 3.00 |
| S34-A9 STS | 3.40 |

The reference variety S40-R9 is assigned factor 1. Soya varieties having a factor greater than 3, preferably greater than 3.5, are suitable as a subsequent crop to maize when weed control in that maize crop has been carried out using HPPD inhibitor herbicides. Soya varieties having a factor between 3 and 2 are less suitable, while soya varieties having a factor of less than 2 are unsuitable. The higher the factor, the better the suitability of the soya variety.

The method according to the invention is not limited in respect of the HPPD inhibitor herbicides used. Examples of compounds of the class of HPPD inhibitors are compounds of formula I

wherein Q is an organic substituent which is so chosen that the compound of formula I has a pK value of from 1 to 5;
T is $T_1$

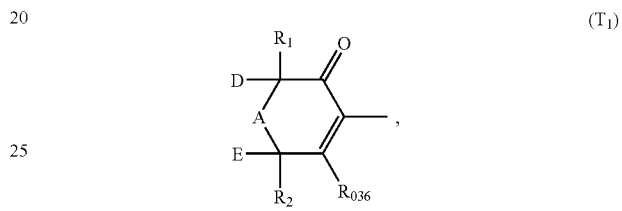

wherein
D is hydrogen or $R_3$;
E is hydrogen or $R_4$; or
D and E together are $C_2$-$C_3$alkylene which can be mono- or poly-substituted by $R_6$;
A is $C_1$-$C_2$alkylene which can be mono- or poly-substituted by $R_5$; or A may additionally be carbonyl, oxygen or —N—$R_7$— when D and E are other than $C_2$-$C_3$alkylene;
$R_1$, $R_2$, $R_3$, $R_4$, $R_5$ and $R_6$ are each independently of the others hydrogen, $C_1$-$C_4$alkyl, phenyl, $C_1$-$C_4$alkoxy, halogen, hydroxy, cyano, hydroxycarbonyl or $C_1$-$C_4$alkoxycarbonyl;
or $R_2$ and $R_4$ together form a $C_2$-$C_4$alkylene chain which can be interrupted by oxygen and/or carbonyl and/or sulfur, with the proviso that the oxygen and sulfur atoms are separated by at least one methylene group;
$R_7$ is $C_1$-$C_4$alkyl, alkoxycarbonyl or $C_1$-$C_4$alkylcarbonyl;
$R_{036}$ is hydroxy, $O^-M^+$, wherein $M^+$ is an alkali metal cation or ammonium cation, halogen, $C_1$-$C_{12}$alkylsufonyloxy, amino, $C_1$-$C_4$alkylthio, $C_1$-$C_{12}$alkylsulfinyl, $C_1$-$C_{12}$alkylsulfonyl, $C_1$-$C_{12}$haloalkylthio, $C_1$-$C_{12}$haloalkylsulfinyl, $C_1$-$C_{12}$haloalkylsulfonyl, $C_1$-$C_6$alkoxy-$C_1$-$C_6$alkylthio, $C_1$-$C_6$alkoxy-$C_1$-$C_6$alkylsulfinyl, $C_1$-$C_6$alkoxy-$C_1$-$C_6$alkylsulfonyl, $C_3$-$C_{12}$alkenylthio, $C_3$-$C_{12}$alkenylsulfinyl, $C_3$-$C_{12}$alkenylsulfonyl, $C_3$-$C_{12}$alkynylthio, $C_3$-$C_{12}$alkynylsulfinyl, $C_3$-$C_{12}$alkynylsulfonyl, $C_1$-$C_4$alkoxycarbonyl-$C_1$-$C_4$alkylthio, $C_1$-$C_4$alkoxycarbonyl-$C_1$-$C_4$alkylsulfinyl, $C_1$-$C_4$alkoxycarbonyl-$C_1$-$C_4$alkylsulfonyl, $(C_1$-$C_4$alkoxy$)_2$P(O)O, $C_1$-$C_4$alkyl-$(C_1$-$C_4$alkoxy)P(O)O, H($C_1$-$C_4$alkoxy)P(O)O, $R_{037}R_{038}$N, $R_{039}R_{040}$NNH, $R_{041}R_{042}$NNC(O)O—, $R_{043}R_{044}$NC(O)NH—, $C_1$-$C_{18}$alkylcarbonyloxy, $C_2$-$C_{18}$alkenylcarbonyloxy, $C_2$-$C_{18}$alkynylcarbonyloxy, $C_3$-$C_6$cycloalkylcarbonyloxy, $C_1$-$C_{12}$alkoxycarbonyloxy, $C_1$-$C_{12}$alkylthiocarbonyloxy or $C_1$-$C_{12}$alkylthiocarbamoyl, wherein the alkyl, alkenyl and alkynyl groups can be substituted by halogen, $C_1$-$C_6$alkoxy, $C_1$-$C_6$alkylthio, $C_1$-$C_6$alkylsulfinyl, $C_1$-$C_6$alkylsulfonyl or by cyano; or $R_{036}$ is phenoxy, phenylthio, phenylsulfinyl, phenylsulfonyl, phenylsulfonylamino, phenylsulfonyloxy, benzoyloxy or benzoyl-$C_1$-$C_6$alkoxy, wherein the phenyl groups may in turn be substituted one or more times by halogen, nitro, cyano, $C_1$-$C_4$alkyl, $C_1$-$C_4$haloalkyl, $C_1$-$C_4$alkoxy and/or $C_1$-$C_4$haloalkoxy, or $R_{036}$ is a group $Het_{07}$-thio, $Het_{08}$-sulfinyl, $Het_{09}$-sulfonyl, $Het_{010}$-(CO)O or $Het_{011}$-N($R_{047}$);

wherein $Het_{07}$, $Het_{08}$, $Het_{09}$, $Het_{010}$ and $Het_{011}$ are each independently of the others a five- to ten-membered monocyclic or annellated bicyclic ring system which may be aromatic or partially saturated and may contain from 1 to 4 hetero atoms selected from nitrogen, oxygen and sulfur, and each ring system may contain not more than two oxygen atoms and not more than two sulfur atoms, and the ring system itself can be substituted by $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, di($C_1$-$C_4$alkyl)aminosulfonyl, di($C_1$-$C_4$alkyl)amino, halogen, cyano, nitro or by phenyl, and the substituents on the nitrogen atom in the heterocyclic ring are other than halogen;

$R_{037}$, $R_{038}$, $R_{039}$, $R_{040}$, $R_{041}$, $R_{042}$, $R_{043}$, $R_{044}$ and $R_{047}$ are each independently of the others hydrogen or $C_1$-$C_6$alkyl; or $R_{037}$ and $R_{038}$ together or $R_{039}$ and $R_{040}$ together or $R_{041}$ and $R_{042}$ together or $R_{043}$ and $R_{044}$ together are pyrrolidino, piperidino, morpholino or thiomorpholino, which can be mono- or poly-substituted by methyl groups;

or T is $T_2$

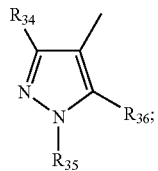

(T$_2$)

wherein $R_{34}$ is hydrogen, $C_1$-$C_4$alkyl, $C_1$-$C_4$haloalkyl, $C_3$-$C_6$cycloalkyl, $C_2$-$C_4$alkenyl, $C_2$-$C_4$alkynyl or benzyl, it being possible for the phenyl group to be substituted one or more times by $C_1$-$C_6$alkyl, $C_1$-$C_6$haloalkyl, $C_1$-$C_6$alkoxy, $C_1$-$C_6$haloalkoxy, halogen, cyano, hydroxy and/or nitro;

$R_{35}$ is hydrogen, $C_1$-$C_4$alkyl, $C_1$-$C_4$haloalkyl, $C_3$-$C_6$cycloalkyl, $C_3$-$C_4$alkenyl, $C_3$-$C_4$alkynyl or benzyl, it being possible for the phenyl group to be substituted one or more times by $C_1$-$C_6$alkyl, $C_1$-$C_6$haloalkyl, $C_1$-$C_6$alkoxy, $C_1$-$C_6$haloalkoxy, halogen, cyano, hydroxy and/or nitro;

$R_{36}$ is hydroxy, $O^-M^+$, wherein $M^+$ is an alkali metal cation or ammonium cation, halogen, $C_1$-$C_{12}$alkylsulfonyloxy, amino, $C_1$-$C_4$alkylthio, $C_1$-$C_{12}$alkylsulfinyl, $C_1$-$C_{12}$alkylsulfonyl, $C_1$-$C_{12}$haloalkylthio, $C_1$-$C_{12}$haloalkylsulfinyl, $C_1$-$C_{12}$haloalkylsulfonyl, $C_1$-$C_6$alkoxy-$C_1$-$C_6$alkylthio, $C_1$-$C_6$alkoxy-$C_1$-$C_6$alkylsulfinyl, $C_1$-$C_6$alkoxy-$C_1$-$C_6$alkylsulfonyl, $C_3$-$C_{12}$alkenylthio, $C_3$-$C_{12}$alkenylsulfinyl, $C_3$-$C_{12}$alkenylsulfonyl, $C_3$-$C_{12}$alkynylthio, $C_3$-$C_{12}$alkynylsulfinyl, $C_3$-$C_{12}$alkynylsulfonyl, $C_1$-$C_4$alkoxycarbonyl-$C_1$-$C_4$alkylthio, $C_1$-$C_4$alkoxycarbonyl-$C_1$-$C_4$alkylsulfinyl, $C_1$-$C_4$alkoxycarbonyl-$C_1$-$C_4$alkylsulfonyl, ($C_1$-$C_4$alkoxy)$_2$P(O)O, $C_1$-$C_4$alkyl-($C_1$-$C_4$alkoxy)P(O)O, H($C_1$-$C_4$alkoxy)P(O)O, $R_{37}R_{38}$N, $R_{39}R_{40}$NNH, $R_{41}R_{42}$NC(O)O—, $R_{43}R_{44}$NC(O)NH—, $C_1$-$C_{18}$alkylcarbonyloxy, $C_2$-$C_{18}$alkenylcarbonyloxy, $C_2$-$C_{18}$alkynylcarbonyloxy, $C_3$-$C_6$cycloalkylcarbonyloxy, $C_1$-$C_{12}$alkoxycarbonyloxy, $C_1$-$C_{12}$alkylthiocarbonyloxy or $C_1$-$C_{12}$alkylthiocarbamoyl, wherein the alkyl, alkenyl and alkynyl groups can be substituted by halogen, $C_1$-$C_6$alkoxy, $C_1$-$C_6$alkylthio, $C_1$-$C_6$alkylsulfinyl, $C_1$-$C_6$alkylsulfonyl or by cyano; or $R_{36}$ is phenoxy, phenylthio, phenylsulfinyl, phenylsulfonyl, phenylsulfonylamino, phenylsulfonyloxy, benzoyloxy or benzoyl-$C_1$-$C_6$alkoxy, it being possible for the phenyl groups in turn to be substituted one or more times by halogen, nitro, cyano, $C_1$-$C_4$alkyl, $C_1$-$C_4$haloalkyl, $C_1$-$C_4$alkoxy and/or $C_1$-$C_4$haloalkoxy, or $R_{36}$ is a group $Het_7$-thio, $Het_8$-sulfinyl, $Het_9$-sulfonyl, $Het_{10}$-(CO)O or $Het_{11}$-N($R_{47}$); wherein $Het_7$, $Het_8$, $Het_9$, $Het_{10}$ and $Het_{11}$ are each independently of the others a five- to ten-membered monocyclic or annellated bicyclic ring system which may be aromatic or partially saturated and may contain from 1 to 4 hetero atoms selected from nitrogen, oxygen and sulfur, and each ring system may contain not more than two oxygen atoms and not more than two sulfur atoms, and the ring system itself can be substituted by $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, di($C_1$-$C_4$alkyl)aminosulfonyl, di($C_1$-$C_4$alkyl)amino, halogen, cyano, nitro or by phenyl, and the substituents on the nitrogen atom in the heterocyclic ring are other than halogen;

$R_{37}$, $R_{38}$, $R_{39}$, $R_{40}$, $R_{41}$, $R_{42}$, $R_{43}$, $R_{44}$ and $R_{47}$ are each independently of the others hydrogen or $C_1$-$C_6$alkyl; or $R_{37}$ and $R_{38}$ together or $R_{39}$ and $R_{40}$ together or $R_{41}$ and $R_{42}$ together or $R_{43}$ and $R_{44}$ together are pyrrolidino, piperidino, morpholino or thiomorpholino, which can be mono- or poly-substituted by methyl groups;

or T is $T_3$

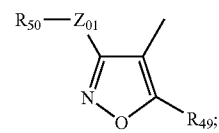

(T$_3$)

wherein $R_{49}$ is $C_1$-$C_4$alkyl, $C_1$-$C_4$haloalkyl, $C_3$-$C_6$cycloalkyl or halo-substituted $C_3$-$C_6$cycloalkyl;

$Z_{01}$ is a chemical bond, S, SO or $SO_2$;

$R_{50}$ is hydrogen or $C_1$-$C_3$alkylene which can be substituted by the following substituents: halogen, hydroxy, $C_1$-$C_6$alkoxy, $C_2$-$C_6$alkenyl, $C_2$-$C_6$alkynyl, $C_3$-$C_6$cycloalkyl, $C_1$-$C_6$alkoxy-$C_1$-$C_6$alkoxy, $C_1$-$C_6$alkoxy-$C_1$-$C_6$alkoxy-$C_1$-$C_6$alkoxy, (3-oxetanyl)-oxy, $C_1$-$C_6$alkyl-substituted (3-oxetanyl)-oxy, benzylthio, benzylsulfinyl, benzylsulfonyl, phenyl, phenoxy, phenylthio, phenylsulfinyl or phenylsulfonyl, it being possible for the phenyl- and benzyl-containing groups in turn to be substituted by one or more $C_1$-$C_6$alkyl, $C_1$-$C_6$haloalkyl, $C_1$-$C_6$alkoxy, $C_1$-$C_6$haloalkoxy, halogen, cyano, hydroxy and/or nitro groups;

or $R_{50}$ is phenyl, it being possible for the phenyl-containing group in turn to be substituted by one or more $C_1$-$C_6$alkyl, $C_1$-$C_6$haloalkyl, $C_1$-$C_6$alkoxy, $C_1$-$C_6$haloalkoxy, halogen, cyano, hydroxy and/or nitro groups, or $R_{50}$ is $C_3$-$C_6$cycloalkyl, $C_1$-$C_6$alkoxy- or $C_1$-$C_6$alkyl-substituted $C_3$-$C_6$cycloalkyl, 3-oxetanyl or $C_1$-$C_6$alkyl-substituted 3-oxetanyl;

or T is $T_4$

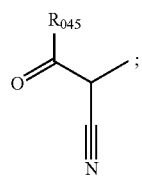

(T4)

wherein $R_{045}$ is $C_1$-$C_6$alkyl, $C_1$-$C_6$haloalkyl, $C_3$-$C_6$cycloalkyl or halo-substituted $C_3$-$C_6$cycloalkyl;

and their agronomically acceptable salts, isomers and enantiomers.

The compounds of formula I also include the salts which the compounds are able to form with amines, alkali metal and alkaline earth metal bases or quaternary ammonium bases. Among the alkali metal and alkaline earth metal hydroxides as salt formers, special mention should be made of the hydroxides of lithium, sodium, potassium, magnesium and calcium, but especially the hydroxides of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Because the compounds of formula I wherein T is $T_1$ are preferably in enolised forms or in the form of salts, formula I also includes the enolised forms of formulae Ia, Ib, Ic and Id wherein M is hydrogen or a metal ion or an ammonium ion.

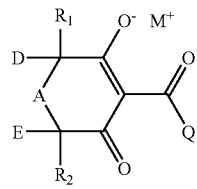

(Ia)

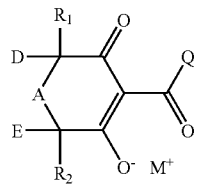

(Ib)

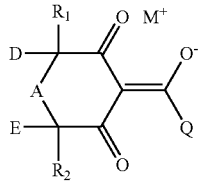

(Ic)

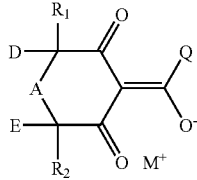

(Id)

Since compounds of formula I may also contain asymmetric carbon atoms, for example in the case of the carbon atom carrying $R_1$, D and A, all stereoisomeric forms are also included.

Q is especially an organic substituent which is so chosen that the compound of formula I has a pK value of from 2.5 to 4.

The organic substituent Q may be an inert substituent of any desired structure, provided that the compounds of formula I retain their action as HPPD inhibitors.

Q is preferably a mono- or poly-substituted phenyl, pyridyl or heteroaryl group, especially 2-benzoyl, 2-isonicotinoyl and 2-nicotinoyl derivatives, the substitution pattern of those groups being freely selectable provided that the compounds of formula I retain their action as HPPD inhibitors.

HPPD inhibitors especially suitable for the method according to the invention are compounds of formula I wherein Q is $Q_1$

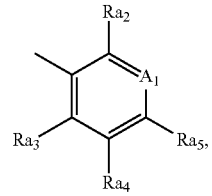

(Q1)

wherein
$A_1$ is methine, $CRa_1$ or $=N-(O)_p$;
p is 0 or 1;
$Ra_1$ is $C_1$-$C_6$alkyl, hydroxy, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_1$-$C_4$alkylcarbonyloxy, $C_1$-$C_4$alkylsulfonyloxy, tosyloxy, $C_1$-$C_4$alkylthio, $C_1$-$C_4$alkylsulfinyl, $C_1$-$C_4$alkylsulfonyl, $C_1$-$C_4$alkylamino, $C_1$-$C_4$dialkylamino, $C_1$-$C_4$alkoxycarbonyl, $C_1$-$C_4$haloalkyl, formyl, cyano, halogen, phenyl or phenoxy; it being possible for phenyl in turn to be substituted by $C_1$-$C_3$alkyl, $C_1$-$C_3$haloalkyl, $C_1$-$C_3$alkoxy, $C_1$-$C_3$haloalkoxy, halogen, cyano and/or by nitro;

or $Ra_1$ is a three- to ten-membered monocyclic ring system or, together with $Ra_2$ or $Ra_5$, an annellated mono- or bi-cyclic ring system which may be interrupted by oxygen, sulfur, SO, $SO_2$, $NRa_6$, carbonyl and/or by =$NORa_7$, the ring system, unless it is annellated, being bonded to the carbon atom of the substituent A directly or by way of a $C_1$-$C_4$alkylene, —CH=CH—, —C≡C—, —$CH_2$O—, —$CH_2$N($C_1$-$C_4$alkyl)-, —$CH_2$S—, —$CH_2$SO—, or —$CH_2SO_2$— group, and the ring system may contain not more than two oxygen atoms and not more than two sulfur atoms, and the ring system can itself be mono-, di- or tri-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_4$alkoxy-$C_1$-$C_2$alkylthio, $C_1$-$C_4$alkylcarbonyl-$C_1$-$C_2$alkylthio, $C_1$-$C_4$alkoxycarbonyl-$C_1$-$C_2$alkylthio, cyano-$C_1$-$C_4$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di($C_1$-$C_2$alkyl)aminosulfonyl, di($C_1$-$C_4$alkyl)amino, halogen, cyano, nitro, phenyl and/or benzylthio, it being possible for phenyl and benzylthio in turn to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and substituents on the nitrogen atom in the heterocyclic ring are other than halogen;

or $Ra_1$ is the group —$X_5$-$X_7$ or the group —$X_6$-$X_5$-$X_7$; wherein $X_6$ is a $C_1$-$C_6$alkylene, $C_3$-$C_6$alkenylene or $C_3$-$C_6$alkynylene chain which can be mono- or poly-substituted by halogen and/or by $X_8$, the unsaturated bonds of the chain not being bonded directly to the substituent $X_5$;

$X_8$ is hydroxy, $C_1$-$C_6$alkoxy, $C_3$-$C_6$cycloalkyloxy, $C_1$-$C_6$alkoxy-$C_1$-$C_6$alkoxy, $C_1$-$C_6$alkoxy-$C_1$-$C_6$alkoxy-$C_1$-$C_6$alkoxy or $C_1$-$C_2$alkylsulfonyloxy;

$X_5$ is oxygen, —O(CO)—, —(CO)O—, —O(CO)O—, —N($C_1$-$C_4$alkyl)-O—, —O—N($C_1$-$C_4$alkyl)-, thio, sulfinyl, sulfonyl, —$SO_2$N($C_1$-$C_4$alkyl)-, —N($C_1$-$C_4$alkoxy)$SO_2$—, —N($C_1$-$C_4$alkyl)$SO_2$—, —N($C_1$-$C_2$alkoxy-$C_1$-$C_2$alkyl)$SO_2$— or —N($C_1$-$C_4$alkyl)-;

$Ra_6$ is hydrogen, $C_1$-$C_4$alkyl, $C_1$-$C_4$alkylthio-$C_1$-$C_4$carbonyl, $C_1$-$C_4$alkylsulfinyl-$C_1$-$C_4$carbonyl, $C_1$-$C_4$alkylsulfonyl-$C_1$-$C_4$carbonyl, $C_1$-$C_4$alkoxycarbonyl, $C_1$-$C_4$alkylcarbonyl, phenylcarbonyl or phenyl, it being possible for the phenyl groups in turn to be substituted by $C_1$-$C_4$alkyl, $C_1$-$C_4$haloalkyl, $C_1$-$C_4$alkoxy, $C_1$-$C_4$haloalkoxy, $C_1$-$C_4$alkylcarbonyl, $C_1$-$C_4$alkoxycarbonyl, $C_1$-$C_4$alkylamino, di-$C_1$-$C_4$alkylamino, $C_1$-$C_4$alkyl-S—, $C_1$-$C_4$alkyl-SO—, $C_1$-$C_4$alkyl-$SO_2$, $C_1$-$C_4$alkyl-S(O)$_2$O, $C_1$-$C_4$haloalkyl-S—, $C_1$-$C_4$haloalkyl-SO, $C_1$-$C_4$haloalkyl-$SO_2$, $C_1$-$C_4$haloalkyl-S(O)$_2$O, $C_1$-$C_4$alkyl-S(O)$_2$NH, $C_1$-$C_4$alkyl-S(O)$_2$N($C_1$-$C_4$alkyl), halogen, nitro or by cyano;

$Ra_7$ is $C_1$-$C_4$alkyl;

$Ra_2$ is hydrogen, $C_1$-$C_6$alkyl, $C_1$-$C_6$haloalkyl, $C_2$-$C_6$alkenyl, $C_2$-$C_6$haloalkenyl, vinyl substituted by $C_1$-$C_2$alkoxycarbonyl or by phenyl, $C_2$-$C_6$alkynyl, $C_2$-$C_6$haloalkynyl, ethynyl substituted by trimethylsilyl, hydroxy, $C_1$-$C_2$alkoxy, $C_1$-$C_2$alkoxycarbonyl or by phenyl, $C_3$-$C_6$allenyl, $C_3$-$C_6$cycloalkyl, halo-substituted $C_3$-$C_6$cycloalkyl, $C_1$-$C_6$alkoxy, $C_3$-$C_6$alkenyloxy, $C_3$-$C_6$alkynyloxy, $C_1$-$C_6$haloalkoxy, $C_3$-$C_6$haloalkenyloxy, cyano-$C_1$-$C_4$alkoxy, $C_1$-$C_4$alkoxy-$C_1$-$C_4$alkoxy, $C_1$-$C_4$alkylthio-$C_1$-$C_4$alkoxy, $C_1$-$C_4$alkylsulfinyl-$C_1$-$C_4$alkoxy, $C_1$-$C_4$alkylsulfonyl-$C_1$-$C_4$alkoxy, $C_1$-$C_4$alkoxycarbonyl-$C_1$-$C_4$alkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_4$alkoxycarbonyl-$C_1$-$C_4$alkylthio, $C_1$-$C_4$alkoxycarbonyl-$C_1$-$C_4$alkylsulfinyl, $C_1$-$C_4$alkoxycarbonyl-$C_1$-$C_4$alkylsulfonyl, benzyl-S—, benzyl-SO—, benzyl-$SO_2$—, $C_1$-$C_6$alkylamino, $C_2$-$C_6$dialkylamino, $C_1$-$C_6$alkylaminosulfonyl, di($C_1$-$C_6$alkylamino)sulfonyl, benzyloxy, benzyl, phenyl, phenoxy, phenylthio, phenylsulfinyl or phenylsulfonyl, it being possible for the phenyl-containing groups in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro, or $Ra_2$ is OS—$C_1$-$C_4$alkyl, OSO—$C_1$-$C_4$alkyl, $OSO_2$—$C_1$-$C_4$alkyl, OS—$C_1$-$C_4$haloalkyl, OSO—$C_1$-$C_4$haloalkyl, $OSO_2$—$C_1$-$C_4$haloalkyl, N($C_1$-$C_4$alkyl)-S—$C_1$-$C_4$alkyl, N($C_1$-$C_4$alkyl)-SO—$C_1$-$C_4$alkyl, N($C_1$-$C_4$alkyl)-$SO_2$—$C_1$-$C_4$alkyl, cyano, carbamoyl, $C_1$-$C_4$alkoxycarbonyl, formyl, halogen, rhodano, amino, hydroxy-$C_1$-$C_4$alkyl, $C_1$-$C_4$alkoxy-$C_1$-$C_4$alkyl, $C_1$-$C_4$alkyl-S—$C_1$-$C_4$alkyl, $C_1$-$C_4$alkyl-SO—$C_1$-$C_4$alkyl, $C_1$-$C_4$alkyl-$SO_2$—$C_1$-$C_4$alkyl, cyano-$C_1$-$C_4$alkyl, $C_1$-$C_6$alkylcarbonyloxy-$C_1$-$C_4$alkyl, $C_1$-$C_4$alkoxycarbonyl-$C_1$-$C_4$alkyl, $C_1$-$C_4$alkoxycarbonyloxy-$C_1$-$C_4$alkyl, $C_1$-$C_4$rhodano-$C_1$-$C_4$alkyl, benzoyloxy-$C_1$-$C_4$alkyl, $C_2$-$C_6$oxiranyl, $C_1$-$C_4$alkylamino-$C_1$-$C_4$alkyl, di($C_1$-$C_4$alkyl)amino-$C_1$-$C_4$alkyl, $C_1$-$C_{12}$alkylthiocarbonyl-$C_1$-$C_4$alkyl or formyl-$C_1$-$C_4$alkyl, or $Ra_2$ is a five- to ten-membered monocyclic or annellated bicyclic ring system which may be aromatic or partially saturated and may contain from 1 to 4 hetero atoms selected from nitrogen, oxygen and sulfur, the ring system being bonded to the pyridine ring by way of a $C_1$-$C_4$alkylene, —CH=CH—, —C≡C—, —$CH_2$O—, —$CH_2$N($C_1$-$C_4$alkyl)-, —$CH_2$SO— or —$CH_2SO_2$— group, and each ring system may contain not more than two oxygen atoms and not more than two sulfur atoms, and the ring system itself can be mono-, di- or tri-substituted by $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_6$haloalkynyl, $C_1$-$C_6$alkoxy, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_2$-$C_5$alkoxyalkylthio, $C_3$-$C_5$acetylalkylthio, $C_3$-$C_6$alkoxycarbonylalkylthio, $C_2$-$C_4$cyanoalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di($C_1$-$C_2$alkyl)aminosulfonyl, di($C_1$-$C_4$alkyl)amino, halogen, cyano, nitro, phenyl and/or by benzylthio, it being possible for phenyl and benzylthio in turn to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and substituents on the nitrogen atom in the heterocyclic ring are other than halogen;

or $Ra_2$ is the group —$X_1$-$X_3$ or the group —$X_2$-$X_1$-$X_3$; wherein $X_2$ is a $C_1$-$C_6$alkylene, $C_3$-$C_6$alkenylene or $C_3$-$C_6$alkynylene chain which can be mono- or poly-substituted by halogen or by $X_4$, the unsaturated bonds of the chain not being bonded directly to the substituent $X_1$;

$X_4$ is hydroxy, $C_1$-$C_6$alkoxy, $C_3$-$C_6$cycloalkyloxy, $C_1$-$C_6$alkoxy-$C_1$-$C_6$alkoxy, $C_1$-$C_6$alkoxy-$C_1$-$C_6$alkoxy-$C_1$-$C_6$alkoxy or $C_1$-$C_2$alkylsulfonyloxy;

$X_1$ is oxygen, —O(CO)—, —(CO)O—, —O(CO)O—, —N($C_1$-$C_4$alkyl)-O—, —O—N($C_1$-$C_4$alkyl)-, thio, sulfinyl, sulfonyl, —$SO_2$N($C_1$-$C_4$alkyl)-, —N($C_1$-$C_4$alkyl)$SO_2$—, —N($C_1$-$C_2$alkoxy-$C_1$-$C_2$alkyl)$SO_2$— or —N($C_1$-$C_4$alkyl)-;

$X_3$ and $X_7$ are each independently of the other a $C_1$-$C_8$alkyl, $C_3$-$C_6$alkenyl or $C_3$-$C_6$alkynyl group which is mono- or poly-substituted by the following substituents: halogen, hydroxy, amino, formyl, nitro, cyano, mercapto, carbamoyl, $C_1$-$C_6$alkoxy, $C_1$-$C_6$alkoxycarbonyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, halo-substituted $C_3$-$C_6$cycloalkyl, $C_3$-$C_6$alkenyloxy, $C_3$-$C_6$alkynyloxy, $C_1$-$C_6$haloalkoxy, $C_3$-$C_6$haloalkenyloxy, cyano-$C_1$-$C_6$alkoxy, $C_1$-$C_6$alkoxy-$C_1$-$C_6$alkoxy, $C_1$-$C_6$alkoxy-$C_1$-$C_6$alkoxy-$C_1$-$C_6$alkoxy, $C_1$-$C_6$alkylthio-$C_1$-$C_6$alkoxy, $C_1$-$C_6$alkylsulfinyl-$C_1$-$C_6$alkoxy, $C_1$-$C_6$alkylsulfonyl-$C_1$-$C_6$alkoxy, $C_1$-$C_6$alkoxycarbonyl-$C_1$-$C_6$alkoxy, $C_1$-$C_6$alkoxycarbonyl, $C_1$-$C_6$alkylcarbonyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, oxiranyl, which can in turn be substituted by $C_1$-$C_6$alkyl, (3-oxetanyl)-oxy, which can in turn be substituted by $C_1$-$C_6$alkyl, benzylthio, benzylsulfinyl, benzylsulfonyl, $C_1$-$C_6$alkylamino, di($C_1$-$C_6$alkyl)amino, $C_1$-$C_4$alkyl-S(O)$_2$O, $C_1$-$C_4$alkyl-N($C_1$-$C_4$alkyl)$SO_2$—, rhodano, phenyl, phenoxy, phenylthio, phenylsulfinyl and/or phenylsulfonyl;

it being possible for the phenyl- or benzyl-containing groups in turn to be substituted by one or more $C_1$-$C_6$alkyl, $C_1$-$C_6$haloalkyl, $C_1$-$C_6$alkoxy, $C_1$-$C_6$haloalkoxy, halogen, cyano, hydroxy and/or nitro groups, or $X_3$ and $X_7$ are each independently of the other phenyl which can be substituted one or more times by $C_1$-$C_6$alkyl, $C_1$-$C_6$haloalkyl, $C_1$-$C_6$alkoxy, $C_1$-$C_6$haloalkoxy, halogen, cyano, hydroxy and/or nitro; or $X_3$ and $X_7$ are each independently of the other $C_3$-$C_6$cycloalkyl, $C_1$-$C_6$alkoxy- or $C_1$-$C_6$alkylsubstituted $C_3$-$C_6$cycloalkyl, 3-oxetanyl or $C_1$-$C_6$alkyl-substituted 3-oxetanyl;

or $X_3$ and $X_7$ are each independently of the other a five- to ten-membered monocyclic or annellated bicyclic ring system which may be aromatic or saturated or partially saturated and may contain from 1 to 4 hetero atoms selected from nitrogen, oxygen and sulfur, the ring system being bonded to the substituent $X_1$ or $X_5$ directly or by way of a $C_1$-$C_4$alkylene, $C_2$-$C_4$alkenyl-$C_1$-$C_4$alkylene, $C_2$-$C_4$alkynyl-$C_1$-$C_4$alkylene, —N($C_1$-$C_4$alkyl)-$C_1$-$C_4$alkylene, —SO—$C_1$-$C_4$alkylene or —$SO_2$—$C_1$-$C_4$alkylene group, and each ring system may contain not more than two oxygen atoms and not more than two sulfur atoms, and the ring system can itself be mono-, di- or tri-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, hydroxy, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_2$-$C_5$alkoxyalkylthio, $C_3$-$C_5$acetylalkylthio, $C_3$-$C_6$alkoxycarbonylalkylthio, $C_2$-$C_4$cyanoalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di($C_1$-$C_2$alkyl)aminosulfonyl, di($C_1$-$C_4$alkyl)amino, halogen, cyano, nitro, phenyl and/or by benzylthio, it being possible for phenyl and benzylthio in turn to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and the substituents on the nitrogen atom in the heterocyclic ring are other than halogen;

$Ra_3$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_6$alkylamino, $C_2$-$C_6$dialkylamino, $C_1$-$C_6$alkylaminosulfonyl, $C_2$-$C_6$dialkylaminosulfonyl, phenyl, phenylthio, phenylsulfinyl, phenylsulfonyl or phenoxy, it being possible for phenyl in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro, or $Ra_3$ is —N($C_1$-$C_4$alkyl)-S—$C_1$-$C_4$alkyl, —N($C_1$-$C_4$alkyl)-SO—$C_1$-$C_4$alkyl, —N($C_1$-$C_4$alkyl)-$SO_2$—$C_1$-$C_4$alkyl, cyano, halogen, amino, $C_1$-$C_4$alkoxy-$C_1$-$C_4$alkyl, $C_1$-$C_4$alkyl-S—$C_1$-$C_4$alkyl, $C_1$-$C_4$alkyl-SO—$C_1$-$C_4$alkyl or $C_1$-$C_4$alkyl-$SO_2$—$C_1$-$C_4$alkyl;

$Ra_4$ is hydrogen, $C_1$-$C_6$alkyl, hydroxy, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_1$-$C_4$alkylcarbonyloxy, $C_1$-$C_4$alkylsulfonyloxy, tosyloxy, $C_1$-$C_4$alkylthio, $C_1$-$C_4$alkylsulfinyl, $C_1$-$C_4$alkylsulfonyl, $C_1$-$C_4$alkylamino, $C_1$-$C_4$-dialkylamino, $C_1$-$C_4$alkoxycarbonyl, $C_1$-$C_4$haloalkyl, formyl, cyano, halogen, phenyl or phenoxy, it being possible for phenyl in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro;

or $Ra_4$ is a five- to ten-membered monocyclic ring system or, with $Ra_3$, an annellated bicyclic ring system which may contain from 1 to 4 hetero atoms selected from nitrogen, oxygen and sulfur, the ring system, unless it is annellated, being bonded to the ring containing the substituent A directly or by way of a $C_1$-$C_4$alkylene, —CH=CH—, —C≡C—, —$CH_2$O—, —$CH_2$N($C_1$-$C_4$alkyl)-, —$CH_2$S—, —$CH_2$SO— or —$CH_2SO_2$— group, and the ring system may contain not more than two oxygen atoms and not more than two sulfur atoms, and the ring system can itself be mono-, di- or tri-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_4$alkoxy-$C_1$-$C_2$alkylthio, $C_1$-$C_4$alkylcarbonyl-$C_1$-$C_2$alkylthio, $C_1$-$C_4$alkoxycarbonyl-$C_1$-$C_2$alkylthio, cyano-$C_1$-$C_4$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di($C_1$-$C_2$alkyl)aminosulfonyl, di($C_1$-$C_4$alkyl)amino, halogen, cyano, nitro, phenyl and/or by benzylthio, it being possible for phenyl and benzylthio in turn to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and substituents on the nitrogen atom in the heterocyclic ring are other than halogen;

$Ra_5$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_6$alkylamino, $C_2$-$C_6$dialkylamino, $C_1$-$C_6$alkylaminosulfonyl, $C_2$-$C_6$dialkylaminosulfonyl, phenyl, phenylthio, phenylsulfinyl, phenylsulfonyl or phenoxy, it being possible for phenyl in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro, or $Ra_5$ is —N($C_1$-$C_4$alkyl)-S—$C_1$-$C_4$alkyl, —N($C_1$-$C_4$alkyl)-SO—$C_1$-$C_4$alkyl, —N($C_1$-$C_4$alkyl)-$SO_2$—$C_1$-$C_4$alkyl, cyano, halogen, amino, $C_1$-$C_4$alkoxy-$C_1$-$C_4$alkyl, $C_1$-$C_4$alkyl-S—$C_1$-$C_4$alkyl, $C_1$-$C_4$alkyl-SO—$C_1$-$C_4$alkyl or $C_1$-$C_4$alkyl-$SO_2$—$C_1$-$C_4$alkyl, and agronomically acceptable salts/N-oxides/isomers/enantiomers of those compounds.

In preferred compounds of formula I, T is $T_1$. Those compounds correspond to formula Iz

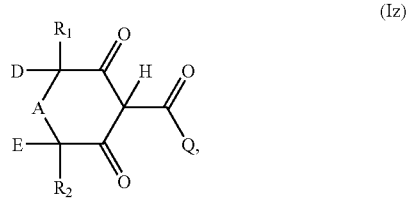

(Iz)

wherein the substituents are as defined for formula I.

The alkyl groups appearing in the above substituent definitions may be straight-chain or branched and are, for example, methyl, ethyl, n-propyl, isopropyl, n-butyl, sec-butyl, isobutyl or tert-butyl. Alkoxy, alkenyl and alkynyl radicals are derived from the mentioned alkyl radicals. The alkenyl and alkynyl groups may be mono- or poly-unsaturated. Alkoxy is, for example, methoxy, ethoxy, propoxy, isopropoxy, n-butoxy, isobutoxy, sec-butoxy or tert-butoxy. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl.

Halogen is generally fluorine, chlorine, bromine or iodine. The same is also true of halogen in conjunction with other meanings, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 1-fluoroethyl, 2-fluoroethyl, 2-chloroethyl, 2-fluoroprop-2-yl, pentafluoroethyl, 1,1-difluoro-2,2,2-trichloroethyl, 2,2,3,3-tetrafluoroethyl and 2,2,2-trichloroethyl, pentafluoroethyl, heptafluoro-n-propyl and perfluoro-n-hexyl.

Alkenyl and alkynyl groups can be mono- or poly-unsaturated, so that alkyl, alkenyl and alkynyl chains having one or more double or triple bonds are also included. Alkenyl is, for example, vinyl, allyl, isobuten-3-yl, $CH_2$=CH—$CH_2$—CH=CH—, $CH_2$=CH—$CH_2$—$CH_2$—CH=CH— or $CH_3$—CH=CH—$CH_2$—CH=CH—. A preferred alkynyl is, for example, propargyl, and a preferred allenyl is $CH_2$=C=$CH_2$—.

An alkylene chain can also be substituted by one or more $C_1$-$C_3$alkyl groups, especially by methyl groups. Such alkylene chains and alkylene groups are preferably unsubstituted. The same applies also to all groups containing $C_3$-$C_6$cycloalkyl, $C_3$-$C_5$oxacycloalkyl, $C_3$-$C_5$thiacycloalkyl, $C_3$-$C_4$dioxacycloalkyl, $C_3$-$C_4$dithiacycloalkyl or $C_3$-$C_4$oxathiacycloalkyl which occur, for example, also as part of oxygen- and sulfur-containing heterocyclic ring systems of the radicals $Ra_1$ and $Ra_2$.

A $C_1$-$C_4$alkylene, $C_1$-$C_4$alkenylene or $C_2$-$C_4$alkynylene chain which may be interrupted by oxygen, —N($C_1$-$C_4$alkyl)-, sulfur, sulfinyl or sulfonyl, or in $X_2$ or $X_6$ in the meaning of a $C_1$-$C_6$alkylene, $C_3$-$C_6$alkenylene or $C_3$-$C_6$alkynylene chain which can be mono- or poly-substituted by halogen or by $X_4$ or $X_8$, and wherein the unsaturated bonds of the chain are not bonded directly to the substituent $X_1$ or $X_5$, is to be understood as being, for example, —$H_2$—, —$CH_2CH_2$—, —$CH_2CH_2CH_2$—, —$CH_2CH_2CH_2CH_2$—, —CH($CH_3$)—, —$CH_2$CH($CH_3$)—, —$CH_2$CH($CH_3$)$CH_2$—, —$CH_2$CH(Cl)$CH_2$—, —$CH_2$CH(O$CH_3$)$CH_2$—, —$CH_2$O—, —O$CH_2$—, —$CH_2$O$CH_2$—, —O$CH_2$$CH_2$—, —O$CH_2$$CH_2$$CH_2$—, —$CH_2$O$CH_2$$CH_2$—, —$CH_2$OCH($CH_3$)$CH_2$—, —S$CH_2$—, —S$CH_2$$CH_2$—, —S$CH_2$$CH_2$$CH_2$—, —$CH_2$S—, —$CH_2$S$CH_2$—, —$CH_2$S(O)$CH_2$—, —$CH_2$$SO_2$$CH_2$—, —$CH_2$S$CH_2$$CH_2$—, —$CH_2$S(O)$CH_2$$CH_2$—, —$CH_2$$SO_2$$CH_2$$CH_2$—, —$CH_2$$SO_2$NH—, —$CH_2$N($CH_3$)$SO_2$$CH_2$$CH_2$—, —N($SO_2$Me)$CH_2$$CH_2$—, —$CH_2$C(O)NH— or —$CH_2$NHC(O)$CH_2$—. A $C_2$-$C_4$alkenylene chain which may be uninterrupted or interrupted by oxygen is accordingly to be understood as being, for example, —CH=CH—$CH_2$—, —CH=CH—$CH_2$$CH_2$— or —CH=CH$CH_2$O$CH_2$—, and a $C_2$-$C_4$alkynylene chain which may be uninterrupted or interrupted by oxygen is to be understood as being, for example, —C≡C—, —C≡C$CH_2$—, —C≡C$CH_2$O—, —C≡C$CH_2$O$CH_2$— or —OC≡C$CH_2$—.

A three- to ten-membered mono- or bi-cyclic ring system $Ra_1$ or $Ra_2$, which may be interrupted once or up to three times selected from oxygen, sulfur, S(O), $SO_2$, N($Ra_6$), carbonyl and C(=NO$Ra_7$) and which is bonded to the carbon atom of the substituent $A_1$ or to the group $Q_1$ or $Q_2$ either directly or by way of a $C_1$-$C_4$alkylene, $C_1$-$C_4$alkenylene or $C_2$-$C_4$alkynylene bridge which may be interrupted by oxygen, —N($C_1$-$C_4$alkyl)-, sulfur, sulfinyl or sulfonyl, is to be understood as being, for example, 1-methyl-1H-pyrazol-3-yl, 1-ethyl-1H-pyrazol-3-yl, 1-propyl-1H-pyrazol-3-yl, 1H-pyrazol-3-yl, 1,5-dimethyl-1H-pyrazol-3-yl, 4-chloro-1-methyl-1H-pyrazol-3-yl, 1H-pyrazol-1-yl, 3-methyl-1H-pyrazol-1-yl, 3,5-dimethyl-1H-pyrazol-1-yl, 3-isoxazolyl, 5-methyl-3-isoxazolyl, 3-methyl-5-isoxazolyl, 5-isoxazolyl, 1H-pyrrol-2-yl, 1-methyl-1H-pyrrol-2-yl, 1H-pyrrol-1-yl, 1-methyl-1H-pyrrol-3-yl, 2-furanyl, 5-methyl-2-furanyl, 3-furanyl, 5-methyl-2-thienyl, 2-thienyl, 3-thienyl, 1-methyl-1H-imidazol-2-yl, 1H-imidazol-2-yl, 1-methyl-1H-imidazol-4-yl, 1-methyl-1H-imidazol-5-yl, 4-methyl-2-oxazolyl, 5-methyl-2-oxazolyl, 2-oxazolyl, 2-methyl-5-oxazolyl, 2-methyl-4-oxazolyl, 4-methyl-2-thiazolyl, 5-methyl-2-thiazolyl, 2-thiazolyl, 2-methyl-5-thiazolyl, 2-methyl-4-thiazolyl, 3-methyl-4-isothiazolyl, 3-methyl-5-isothiazolyl, 5-methyl-3-isothiazolyl, 1-methyl-1H-1,2,3-triazol-4-yl, 2-methyl-2H-1,2,3-triazol-4-yl, 4-methyl-2H-1,2,3-triazol-2-yl, 1-methyl-1H-1,2,4-triazol-3-yl, 1,5-dimethyl-1H-1,2,4-triazol-3-yl, 3-methyl-1H-1,2,4-triazol-1-yl, 5-methyl-1H-1,2,4-triazol-1-yl, 4,5-dimethyl-4H-1,2,4-triazol-3-yl, 4-methyl-4H-1,2,4-triazol-3-yl, 4H-1,2,4-triazol-4-yl, 5-methyl-1,2,3-oxadiazol-4-yl, 1,2,3-oxadiazol-4-yl, 3-methyl-1,2,4-oxadiazol-5-yl, 5-methyl-1,2,4-oxadiazol-3-yl, 4-methyl-3-furazanyl, 3-furazanyl, 5-methyl-1,2,4-oxadiazol-2-yl, 5-methyl-1,2,3-thiadiazol-4-yl, 1,2,3-thiadiazol-4-yl, 3-methyl-1,2,4-thiadiazol-5-yl, 5-methyl-1,2,4-thiadiazol-3- yl, 4-methyl-1,2,5-thiadiazol-3-yl, 5-methyl-1,3,4-thiadiazol-2-yl, 1-methyl-1H-tetrazol-5-yl, 1H-tetrazol-5-yl, 5-methyl-1H-tetrazol-1-yl, 2-methyl-2H-tetrazol-5-yl, 2-ethyl-2H-tetrazol-5-yl, 5-methyl-2H-tetrazol-2-yl, 2H-tetrazol-2-yl, 2-pyridinyl, 6-methyl-2-pyridinyl, 4-pyridinyl, 3-pyridinyl, 6-methyl-3-pyridazinyl, 5-methyl-3-pyridazinyl, 3-pyridazinyl, 4,6-dimethyl-2-pyrimidinyl, 4-methyl-2-pyrimidinyl, 2-pyrimidinyl, 2-methyl-4-pyrimidinyl, 2-chloro-4-pyrimidinyl, 2,6-dimethyl-4-pyrimidinyl, 4-pyrimidinyl, 2-methyl-5-pyrimidinyl, 6-methyl-2-pyrazinyl, 2-pyrazinyl, 4,6-dimethyl-1,3,5-triazin-2-yl, 4,6-dichloro-1,3,5-triazin-2-yl, 1,3,5-triazin-2-yl, 4methyl-1,3,5-triazin-2-yl, 3-methyl-1,2,4-triazin-5-yl, 3-methyl-1,2,4-triazin-6-yl,

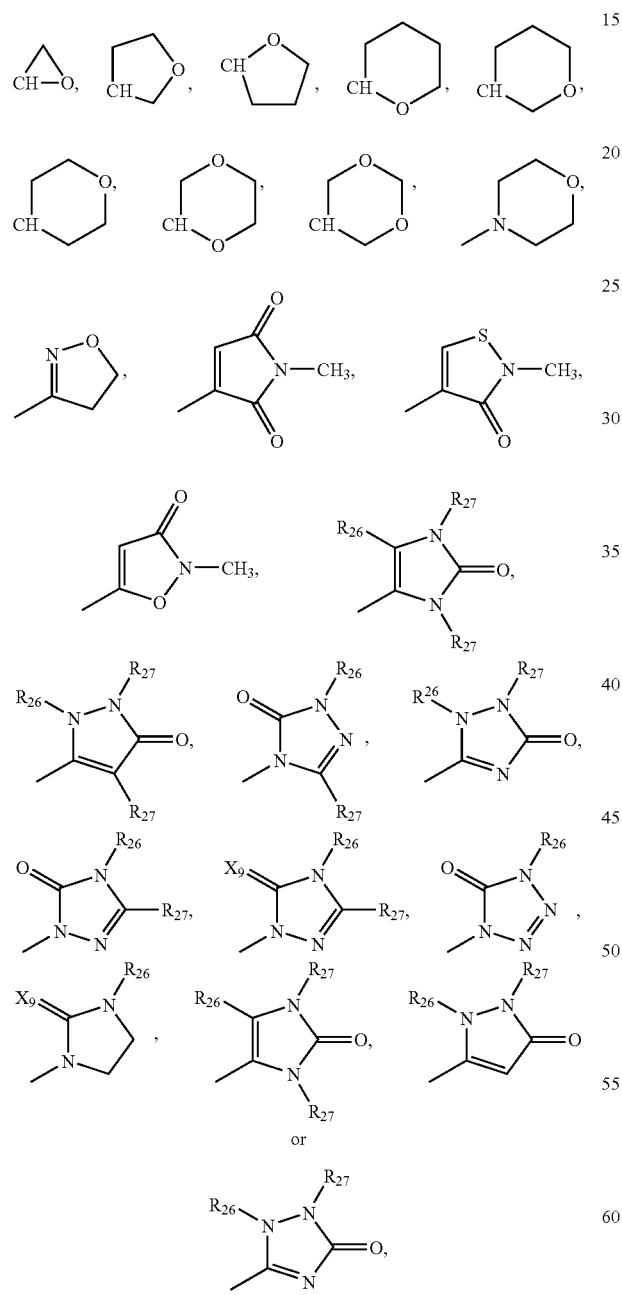

wherein each $R_{26}$ is methyl, each $R_{27}$ independently is hydrogen, $C_1$-$C_3$alkyl, $C_1$-$C_3$alkoxy, $C_1$-$C_3$alkylthio or trifluoromethyl, and $X_9$ is oxygen or sulfur.

A further annellated (fused-on), monocyclic or bicyclic ring system which is formed, for example, by two adjacent substituents $Ra_1$ and $Ra_2$ or $Ra_1$ and $Ra_5$ and which is uninterrupted or interrupted once or up to three times selected from oxygen, sulfur, S(O), $SO_2$, —N($Ra_6$)—, carbonyl and C(=NO$Ra_7$) and which may be additionally substituted by one or more substituents is to be understood as being, for example, an annellated, bidentate ring system of formula

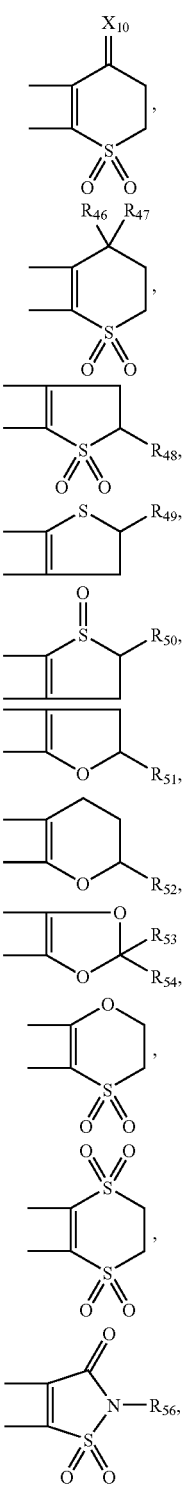

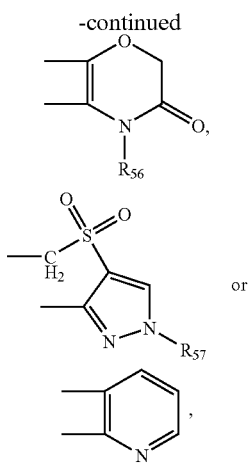

wherein especially $R_{46}$ is hydrogen, halogen, $C_1$-$C_4$alkyl, $C_1$-$C_4$haloalkyl, $C_1$-$C_4$alkoxy or $C_1$-$C_4$alkylthio; $R_{47}$ is hydrogen, halogen, $C_1$-$C_4$alkyl or $C_1$-$C_4$alkoxy; and $R_{50}$, $R_{51}$, $R_{52}$, $R_{53}$, $R_{54}$, $R_{55}$, $R_{56}$, $R_{57}$, $R_{58}$ and $R_{59}$ are hydrogen or $C_1$-$C_4$alkyl; and $X_{10}$ is oxygen or $NOR_{59}$.

HPPD Inhibitors of formula I are described, for example, in WO/0015615, WO 00/37437, WO 01/66522 and WO 01/94339.

Compounds of formula I that are well suited to the method according to the invention are those wherein T is $T_1$;
$R_1$ and $R_2$ are hydrogen;
A is $C_1$-$C_2$alkylene;
D and E together are $C_2$-$C_3$alkylene;
Q is $Q_1$, wherein
$A_1$ is methine, $CRa_1$ or =N—(O)$_p$, but preferably =N—(O)$_p$;
p is 0;
$Ra_1$ is hydrogen, $C_1$-$C_6$alkyl, hydroxy, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_1$-$C_4$alkylcarbonyloxy, $C_1$-$C_4$alkylsulfonyloxy, tosyloxy, $C_1$-$C_4$alkylthio, $C_1$-$C_4$alkylsulfinyl, $C_1$-$C_4$alkylsulfonyl, $C_1$-$C_4$alkylamino, $C_1$-$C_4$dialkylamino, $C_1$-$C_4$alkoxycarbonyl, $C_1$-$C_4$haloalkyl, formyl, cyano, halogen, phenyl or phenoxy; it being possible for phenyl in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro;
$Ra_2$ is hydrogen, $C_1$-$C_6$alkyl, $C_1$-$C_6$haloalkyl, $C_2$-$C_6$alkenyl, $C_2$-$C_6$haloalkenyl, vinyl substituted by $C_1$-$C_2$alkoxycarbonyl or by phenyl, $C_2$-$C_6$alkynyl, $C_2$-$C_6$haloalkynyl, ethynyl substituted by trimethylsilyl, hydroxy, $C_1$-$C_2$alkoxy, $C_1$-$C_2$alkoxycarbonyl or by phenyl, $C_3$-$C_6$allenyl, $C_3$-$C_6$cycloalkyl, halo-substituted $C_3$-$C_6$cycloalkyl, $C_1$-$C_6$alkoxy, $C_3$-$C_6$alkenyloxy, $C_3$-$C_6$alkynyloxy, $C_1$-$C_6$haloalkoxy, $C_3$-$C_6$haloalkenyloxy, cyano-$C_1$-$C_4$alkoxy, $C_1$-$C_4$alkoxy-$C_1$-$C_4$alkoxy, $C_1$-$C_4$alkylthio-$C_1$-$C_4$alkoxy, $C_1$-$C_4$alkylsulfinyl-$C_1$-$C_4$alkoxy, $C_1$-$C_4$alkylsulfonyl-$C_1$-$C_4$alkoxy, $C_1$-$C_4$alkoxycarbonyl-$C_1$-$C_4$alkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_4$alkoxycarbonyl-$C_1$-$C_4$alkylthio, $C_1$-$C_4$alkoxycarbonyl-$C_1$-$C_4$alkylsulfinyl, $C_1$-$C_4$alkoxycarbonyl-$C_1$-$C_4$alkylsulfonyl, benzyl-S—, benzyl-SO—, benzyl-SO$_2$—, $C_1$-$C_6$alkylamino, $C_2$-$C_6$dialkylamino, $C_1$-$C_6$alkylaminosulfonyl, di($C_1$-$C_6$alkylamino)sulfonyl, benzyloxy, benzyl, phenyl, phenoxy, phenylthio, phenylsulfinyl or phenylsulfonyl, it being possible for the phenyl-containing groups in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro, or $Ra_2$ is OS—$C_1$-$C_4$alkyl, OSO—$C_1$-$C_4$alkyl, OSO$_2$—$C_1$-$C_4$alkyl, OS—$C_1$-$C_4$haloalkyl, OSO—$C_1$-$C_4$haloalkyl, OSO$_2$—$C_1$-$C_4$haloalkyl, N($C_1$-$C_4$alkyl)-S—$C_1$-$C_4$alkyl, N($C_1$-$C_4$alkyl)-SO—$C_1$-$C_4$alkyl, N($C_1$-$C_4$alkyl)-SO$_2$—$C_1$-$C_4$alkyl, cyano, carbamoyl, $C_1$-$C_4$alkoxycarbonyl, formyl, halogen, rhodano, amino, hydroxy-$C_1$-$C_4$alkyl, $C_1$-$C_4$alkoxy-$C_1$-$C_4$alkyl, $C_1$-$C_4$alkyl-S—$C_1$-$C_4$alkyl, $C_1$-$C_4$alkyl-SO—$C_1$-$C_4$alkyl, $C_1$-$C_4$alkyl-SO$_2$—$C_1$-$C_4$alkyl, cyano-$C_1$-$C_4$alkyl, $C_1$-$C_6$alkylcarbonyloxy-$C_1$-$C_4$alkyl, $C_1$-$C_4$alkoxycarbonyl-$C_1$-$C_4$alkyl, $C_1$-$C_4$alkoxycarbonyloxy-$C_1$-$C_4$alkyl, $C_1$-$C_4$rhodano-$C_1$-$C_4$alkyl, benzoyloxy-$C_1$-$C_4$alkyl, $C_2$-$C_6$oxiranyl, $C_1$-$C_4$alkylamino-$C_1$-$C_4$alkyl, di($C_1$-$C_4$alkyl)amino-$C_1$-$C_4$alkyl, $C_1$-$C_{12}$alkylthiocarbonyl-$C_1$-$C_4$alkyl or formyl-$C_1$-$C_4$alkyl, or $Ra_2$ is the group —$X_1$-$X_3$ or the group —$X_2$-$X_1$-$X_3$; wherein $X_1$, $X_2$ and $X_3$ are as defined above; $Ra_3$ and $Ra_4$ are hydrogen and $Ra_5$ is as defined above.

Compounds of formula I that are especially well suited to the method according to the invention are those wherein
T is $T_1$;
$R_1$ and $R_2$ are hydrogen, A is methylene, D and E together are ethylene, $A_1$ is =N—(O)$_p$;
wherein p is 0;
Q is $Q_1$, $Ra_3$ and $Ra_4$ are hydrogen, $Ra_5$ is $C_1$-$C_3$haloalkyl, especially trifluoromethyl, and $Ra_2$ is $C_1$-$C_4$alkoxy-$C_1$-$C_4$alkoxy-$C_1$-$C_4$alkyl, especially methoxyethoxymethyl.

Further compounds of formula I that are especially well suited to the method according to the invention are listed in the following Tables:

In the Tables, CCH is the ethynyl group, Ph is the phenyl group and Me is the methyl group.

TABLE 1

Compounds of formula Ie

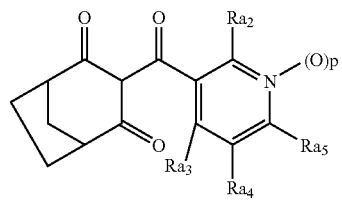

(Ie)

| Comp. No. | $Ra_2$ | $Ra_5$ | $Ra_4$ | $Ra_3$ | p |
|---|---|---|---|---|---|
| 1.001 | H | $CF_3$ | H | H | 0 |
| 1.002 | F | $CF_3$ | H | H | 0 |
| 1.003 | Cl | $CF_3$ | H | H | 0 |
| 1.004 | Br | $CF_3$ | H | H | 0 |
| 1.005 | $CHF_2$ | $CF_3$ | H | H | 0 |
| 1.006 | $CCl_3$ | $CF_3$ | H | H | 0 |
| 1.007 | $CClF_2$ | $CF_3$ | H | H | 0 |
| 1.008 | $CH_3$ | $CF_3$ | H | H | 0 |
| 1.009 | $CH_3$ | $CF_3$ | H | H | 0 |
| 1.01 | $CH_2CH_3$ | $CF_3$ | H | H | 0 |
| 1.011 | $CH(CH_3)_2$ | $CF_3$ | H | H | 0 |
| 1.012 | $(CH_2)_2CH_3$ | $CF_3$ | H | H | 0 |
| 1.013 | $C(CH_3)_3$ | $CF_3$ | H | H | 0 |
| 1.014 | Ph | $CF_3$ | H | H | 0 |
| 1.015 | $CH_2F$ | $CF_3$ | H | H | 0 |
| 1.016 | $CH_2Cl$ | $CF_3$ | H | H | 0 |

TABLE 1-continued

Compounds of formula Ie

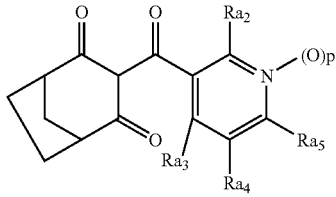

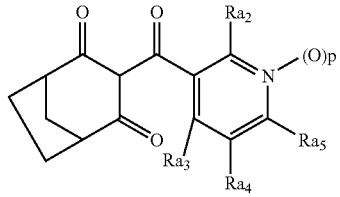

| Comp. No. | $Ra_2$ | $Ra_5$ | $Ra_4$ | $Ra_3$ | p |
|---|---|---|---|---|---|
| 1.017 | $CH_2Br$ | $CF_3$ | H | H | 0 |
| 1.018 | $CH_2OH$ | $CF_3$ | H | H | 0 |
| 1.019 | $CH_2OCOCH_3$ | $CF_3$ | H | H | 0 |
| 1.02 | $CH_2OCOPh$ | $CF_3$ | H | H | 0 |
| 1.021 | $CH_2OCH_3$ | $CF_3$ | H | H | 0 |
| 1.022 | $CH_2OCH_2CH_3$ | $CF_3$ | H | H | 0 |
| 1.023 | $CH_2CH_2OCH_3$ | $CF_3$ | H | H | 0 |
| 1.024 | $CH_2SMe$ | $CF_3$ | H | H | 0 |
| 1.025 | $CH_2SOMe$ | $CF_3$ | H | H | 0 |
| 1.026 | $CH_2SO_2Me$ | $CF_3$ | H | H | 0 |
| 1.027 | $CH_2SO_2Ph$ | $CF_3$ | H | H | 0 |
| 1.028 | $SCH_2Ph$ | $CF_3$ | H | H | 0 |
| 1.029 | $SOCH_2Ph$ | $CF_3$ | H | H | 0 |
| 1.03 | $SO_2CH_2Ph$ | $CF_3$ | H | H | 0 |
| 1.031 | $SCH_3$ | $CF_3$ | H | H | 0 |
| 1.032 | $SOCH_3$ | $CF_3$ | H | H | 0 |
| 1.033 | $SO_2CH_3$ | $CF_3$ | H | H | 0 |
| 1.034 | SPh | $CF_3$ | H | H | 0 |
| 1.035 | SOPh | $CF_3$ | H | H | 0 |
| 1.036 | $SO_2Ph$ | $CF_3$ | H | H | 0 |
| 1.037 | $N(CH_3)_2$ | $CF_3$ | H | H | 0 |
| 1.038 | $CH=CH_2$ | $CF_3$ | H | H | 0 |
| 1.039 | $CH_2CH=CH_2$ | $CF_3$ | H | H | 0 |
| 1.04 | $SO_2N(CH_3)_2$ | $CF_3$ | H | H | 0 |
| 1.041 | Ethynyl | $CF_3$ | H | H | 0 |
| 1.042 | Cyclopropyl | $CF_3$ | H | H | 0 |
| 1.043 | $OCH_3$ | $CF_3$ | H | H | 0 |
| 1.044 | OPh | $CF_3$ | H | H | 0 |
| 1.045 | $OCHF_2$ | $CF_3$ | H | H | 0 |
| 1.046 | $CO_2Me$ | $CF_3$ | H | H | 0 |
| 1.047 | 2-Furyl | $CF_3$ | H | H | 0 |
| 1.048 | $OCH_2$ethynyl | $CF_3$ | H | H | 0 |
| 1.049 | 2-Pyridyl | $CF_3$ | H | H | 0 |
| 1.05 | 3-Pyridyl | $CF_3$ | H | H | 0 |
| 1.051 | 4-Pyridyl | $CF_3$ | H | H | 0 |
| 1.052 | H | $CF_3$ | H | H | 1 |
| 1.053 | F | $CF_3$ | H | H | 1 |
| 1.054 | Cl | $CF_3$ | H | H | 1 |
| 1.055 | Br | $CF_3$ | H | H | 1 |
| 1.056 | $CHF_2$ | $CF_3$ | H | H | 1 |
| 1.057 | $CCl_3$ | $CF_3$ | H | H | 1 |
| 1.058 | $CClF_2$ | $CF_3$ | H | H | 1 |
| 1.059 | $CF_3$ | $CF_3$ | H | H | 1 |
| 1.06 | $CH_3$ | $CF_3$ | H | H | 1 |
| 1.061 | $CH_2CH_3$ | $CF_3$ | H | H | 1 |
| 1.062 | $CH(CH_3)_2$ | $CF_3$ | H | H | 1 |
| 1.063 | $(CH_2)_2CH_3$ | $CF_3$ | H | H | 1 |
| 1.064 | $C(CH_3)_3$ | $CF_3$ | H | H | 1 |
| 1.065 | Ph | $CF_3$ | H | H | 1 |
| 1.066 | $CH_2F$ | $CF_3$ | H | H | 1 |
| 1.067 | $CH_2Cl$ | $CF_3$ | H | H | 1 |
| 1.068 | $CH_2Br$ | $CF_3$ | H | H | 1 |
| 1.069 | $CH_2OH$ | $CF_3$ | H | H | 1 |
| 1.07 | $CH_2OCOCH_3$ | $CF_3$ | H | H | 1 |
| 1.071 | $CH_2OCOPh$ | $CF_3$ | H | H | 1 |
| 1.072 | $CH_2OCH_3$ | $CF_3$ | H | H | 1 |
| 1.073 | $CH_2OCH_2CH_3$ | $CF_3$ | H | H | 1 |
| 1.074 | $CH_2CH_2OCH_3$ | $CF_3$ | H | H | 1 |
| 1.075 | $CH_2SMe$ | $CF_3$ | H | H | 1 |
| 1.076 | $CH_2SOMe$ | $CF_3$ | H | H | 1 |
| 1.077 | $CH_2SO_2Me$ | $CF_3$ | H | H | 1 |
| 1.078 | $CH_2SO_2Ph$ | $CF_3$ | H | H | 1 |
| 1.079 | $SCH_2Ph$ | $CF_3$ | H | H | 1 |
| 1.08 | $SOCH_2Ph$ | $CF_3$ | H | H | 1 |
| 1.081 | $SO_2CH_2Ph$ | $CF_3$ | H | H | 1 |
| 1.082 | $SCH_3$ | $CF_3$ | H | H | 1 |
| 1.083 | $SOCH_3$ | $CF_3$ | H | H | 1 |
| 1.084 | $SO_2CH_3$ | $CF_3$ | H | H | 1 |
| 1.085 | SPh | $CF_3$ | H | H | 1 |
| 1.086 | SOPh | $CF_3$ | H | H | 1 |
| 1.087 | $SO_2Ph$ | $CF_3$ | H | H | 1 |
| 1.088 | $N(CH_3)_2$ | $CF_3$ | H | H | 1 |
| 1.089 | $CH=CH_2$ | $CF_3$ | H | H | 1 |
| 1.09 | $CH_2CH=CH_2$ | $CF_3$ | H | H | 1 |
| 1.091 | $SO_2N(CH_3)_2$ | $CF_3$ | H | H | 1 |
| 1.092 | Ethynyl | $CF_3$ | H | H | 1 |
| 1.093 | Cyclopropyl | $CF_3$ | H | H | 1 |
| 1.094 | $OCH_3$ | $CF_3$ | H | H | 1 |
| 1.095 | OPh | $CF_3$ | H | H | 1 |
| 1.096 | $OCHF_2$ | $CF_3$ | H | H | 1 |
| 1.097 | $CO_2Me$ | $CF_3$ | H | H | 1 |
| 1.098 | 2-Furyl | $CF_3$ | H | H | 1 |
| 1.099 | $OCH_2CCH$ | $CF_3$ | H | H | 1 |
| 1.1 | 2-Pyridyl | $CF_3$ | H | H | 1 |
| 1.101 | 3-Pyridyl | $CF_3$ | H | H | 1 |
| 1.102 | 4-Pyridyl | $CF_3$ | H | H | 1 |
| 1.103 | H | $CF_2CF_3$ | H | H | 0 |
| 1.104 | Cl | $CF_2CF_3$ | H | H | 0 |
| 1.105 | $CHF_2$ | $CF_2CF_3$ | H | H | 0 |
| 1.106 | $CCl_3$ | $CF_2CF_3$ | H | H | 0 |
| 1.107 | $CClF_2$ | $CF_2CF_3$ | H | H | 0 |
| 1.108 | $CF_3$ | $CF_2CF_3$ | H | H | 0 |
| 1.109 | $CH_3$ | $CF_2CF_3$ | H | H | 0 |
| 1.11 | $CH_2CH_3$ | $CF_2CF_3$ | H | H | 0 |
| 1.111 | $CH(CH_3)_2$ | $CF_2CF_3$ | H | H | 0 |
| 1.112 | $(CH_2)_2CH_3$ | $CF_2CF_3$ | H | H | 0 |
| 1.113 | $C(CH_3)_3$ | $CF_2CF_3$ | H | H | 0 |
| 1.114 | $CH_2F$ | $CF_2CF_3$ | H | H | 0 |
| 1.115 | $CH_2Cl$ | $CF_2CF_3$ | H | H | 0 |
| 1.116 | $CH_2OH$ | $CF_2CF_3$ | H | H | 0 |
| 1.117 | $CH_2OCOCH_3$ | $CF_2CF_3$ | H | H | 0 |
| 1.118 | $CH_2OCOPh$ | $CF_2CF_3$ | H | H | 0 |
| 1.119 | $CH_2OCH_3$ | $CF_2CF_3$ | H | H | 0 |
| 1.12 | $CH_2OCH_2CH_3$ | $CF_2CF_3$ | H | H | 0 |
| 1.121 | $CH_2SMe$ | $CF_2CF_3$ | H | H | 0 |
| 1.122 | $CH_2SOMe$ | $CF_2CF_3$ | H | H | 0 |
| 1.123 | $CH_2SO_2Me$ | $CF_2CF_3$ | H | H | 0 |
| 1.124 | $CH_2SO_2Ph$ | $CF_2CF_3$ | H | H | 0 |
| 1.125 | $N(CH_3)_2$ | $CF_2CF_3$ | H | H | 0 |
| 1.126 | $CH=CH_2$ | $CF_2CF_3$ | H | H | 0 |
| 1.127 | $CH_2CH=CH_2$ | $CF_2CF_3$ | H | H | 0 |
| 1.128 | $SO_2N(CH_3)_2$ | $CF_2CF_3$ | H | H | 0 |
| 1.129 | CCH | $CF_2CF_3$ | H | H | 0 |
| 1.13 | Cyclopropyl | $CF_2CF_3$ | H | H | 0 |
| 1.131 | OPh | $CF_2CF_3$ | H | H | 0 |
| 1.132 | $OCH_3$ | $CF_2CF_3$ | H | H | 0 |
| 1.133 | $CO_2Me$ | $CF_2CF_3$ | H | H | 0 |
| 1.134 | $OCH_2CCH$ | $CF_2CF_3$ | H | H | 0 |
| 1.135 | 2-Pyridyl | $CF_2CF_3$ | H | H | 0 |
| 1.136 | 3-Pyridyl | $CF_2CF_3$ | H | H | 0 |
| 1.137 | 4-Pyridyl | $CF_2CF_3$ | H | H | 0 |
| 1.138 | H | $CF_2CF_3$ | H | H | 1 |
| 1.139 | Cl | $CF_2CF_3$ | H | H | 1 |
| 1.14 | $CHF_2$ | $CF_2CF_3$ | H | H | 1 |
| 1.141 | $CCl_3$ | $CF_2CF_3$ | H | H | 1 |
| 1.142 | $CClF_2$ | $CF_2CF_3$ | H | H | 1 |

TABLE 1-continued

Compounds of formula Ie

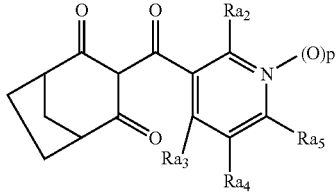
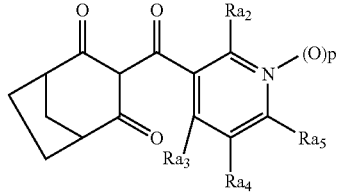

(Ie)

| Comp. No. | Ra₂ | Ra₅ | Ra₄ | Ra₃ | p |
|---|---|---|---|---|---|
| 1.143 | CF₃ | CF₂CF₃ | H | H | 1 |
| 1.144 | CH₃ | CF₂CF₃ | H | H | 1 |
| 1.145 | CH₂CH₃ | CF₂CF₃ | H | H | 1 |
| 1.146 | CH(CH₃)₂ | CF₂CF₃ | H | H | 1 |
| 1.147 | (CH₂)₂CH₃ | CF₂CF₃ | H | H | 1 |
| 1.148 | C(CH₃)₃ | CF₂CF₃ | H | H | 1 |
| 1.149 | CH₂F | CF₂CF₃ | H | H | 1 |
| 1.15 | CH₂Cl | CF₂CF₃ | H | H | 1 |
| 1.151 | CH₂OH | CF₂CF₃ | H | H | 1 |
| 1.152 | CH₂OCOCH₃ | CF₂CF₃ | H | H | 1 |
| 1.153 | CH₂OCOPh | CF₂CF₃ | H | H | 1 |
| 1.154 | CH₂OCH₃ | CF₂CF₃ | H | H | 1 |
| 1.155 | CH₂OCH₂CH₃ | CF₂CF₃ | H | H | 1 |
| 1.156 | CH₂SMe | CF₂CF₃ | H | H | 1 |
| 1.157 | CH₂SOMe | CF₂CF₃ | H | H | 1 |
| 1.158 | CH₂SO₂Me | CF₂CF₃ | H | H | 1 |
| 1.159 | CH₂SO₂Ph | CF₂CF₃ | H | H | 1 |
| 1.16 | N(CH3)2 | CF2CF₃ | H | H | 1 |
| 1.161 | CH=CH₂ | CF₂CF₃ | H | H | 1 |
| 1.162 | CH₂CH=CH₂ | CF₂CF₃ | H | H | 1 |
| 1.163 | SO₂N(CH₃)₂ | CF₂CF₃ | H | H | 1 |
| 1.164 | CCH | CF₂CF₃ | H | H | 1 |
| 1.165 | Cyclopropyl | CF₂CF₃ | H | H | 1 |
| 1.166 | OPh | CF₂CF₃ | H | H | 1 |
| 1.167 | OCH₃ | CF₂CF₃ | H | H | 1 |
| 1.168 | CO₂Me | CF₂CF₃ | H | H | 1 |
| 1.169 | OCH₂CCH | CF₂CF₃ | H | H | 1 |
| 1.17 | 2-Pyridyl | CF₂CF₃ | H | H | 1 |
| 1.171 | 3-Pyridyl | CF₂CF₃ | H | H | 1 |
| 1.172 | 4-Pyridyl | CF₂CF₃ | H | H | 1 |
| 1.173 | H | CF₂CF₂CF₃ | H | H | 0 |
| 1.174 | CHF₂ | CF₂CF₂CF₃ | H | H | 0 |
| 1.175 | CF₃ | CF₂CF₂CF₃ | H | H | 0 |
| 1.176 | CH₃ | CF₂CF₂CF₃ | H | H | 0 |
| 1.177 | CH₂CH₃ | CF₂CF₂CF₃ | H | H | 0 |
| 1.178 | (CH₂)₂CH₃ | CF₂CF₂CF₃ | H | H | 0 |
| 1.179 | CH2Cl | CF₂CF₂CF₃ | H | H | 0 |
| 1.18 | CH₂OCH₃ | CF₂CF₂CF₃ | H | H | 0 |
| 1.181 | H | CF₂CF₂CF₃ | H | H | 1 |
| 1.182 | CHF₂ | CF₂CF₂CF₃ | H | H | 1 |
| 1.183 | CF₃ | CF₂CF₂CF₃ | H | H | 1 |
| 1.184 | CH₃ | CF₂CF₂CF₃ | H | H | 1 |
| 1.185 | CH₂CH₃ | CF₂CF₂CF₃ | H | H | I |
| 1.186 | (CH₂)₂CH₃ | CF₂CF₂CF₃ | H | H | 0 |
| 1.187 | CH₂Cl | CF₂CF₂CF₃ | H | H | 1 |
| 1.188 | CH₂OCH₃ | CF₂CF₂CF₃ | H | H | 1 |
| 1.189 | H | CF₂Cl | H | H | 0 |
| 1.19 | Cl | CF₂Cl | H | H | 0 |
| 1.191 | CHF₂ | CF₂Cl | H | H | 0 |
| 1.192 | CCl₃ | CF₂Cl | H | H | 0 |
| 1.193 | CClF₂ | CF₂Cl | H | H | 0 |
| 1.194 | CF₃ | CF₂Cl | H | H | 0 |
| 1.195 | CH₃ | CF₂Cl | H | H | 0 |
| 1.196 | CH₂CH₃ | CF₂Cl | H | H | 0 |
| 1.197 | CH(CH₃)₂ | CF₂Cl | H | H | 0 |
| 1.198 | (CH₂)₂CH₃ | CF₂Cl | H | H | 0 |
| 1.199 | C(CH₃)₃ | CF₂Cl | H | H | 0 |
| 1.2 | CH₂F | CF₂Cl | H | H | 0 |
| 1.201 | CH₂Cl | CF₂Cl | H | H | 0 |
| 1.202 | CH₂OH | CF₂Cl | H | H | 0 |
| 1.203 | CH₂OCOCH₃ | CF₂Cl | H | H | 0 |
| 1.204 | CH₂OCOPh | CF₂Cl | H | H | 0 |
| 1.205 | CH₂OCH₃ | CF₂Cl | H | H | 0 |
| 1.206 | CH₂OCH₂CH₃ | CF₂Cl | H | H | 0 |
| 1.207 | CH₂SMe | CF₂Cl | H | H | 0 |
| 1.208 | CH₂SOMe | CF₂Cl | H | H | 0 |
| 1.209 | CH₂SO₂Me | CF₂Cl | H | H | 0 |
| 1.21 | CH₂SO₂Ph | CF₂Cl | H | H | 0 |
| 1.211 | N(CH₃)₂ | CF₂Cl | H | H | 0 |
| 1.212 | CH=CH₂ | CF₂Cl | H | H | 0 |
| 1.213 | CH₂CH=CH₂ | CF₂Cl | H | H | 0 |
| 1.214 | SO₂N(CH₃)₂ | CF₂Cl | H | H | 0 |
| 1.215 | CCH | CF₂Cl | H | H | 0 |
| 1.216 | Cyclopropyl | CF₂Cl | H | H | 0 |
| 1.217 | OPh | CF₂Cl | H | H | 0 |
| 1.218 | OCH₃ | CF₂Cl | H | H | 0 |
| 1.219 | CO₂Me | CF₂Cl | H | H | 0 |
| 1.22 | OCH₂CCH | CF₂Cl | H | H | 0 |
| 1.221 | 2-Pyridyl | CF₂Cl | H | H | 0 |
| 1.222 | 3-Pyridyl | CF₂Cl | H | H | 0 |
| 1.223 | 4-Pyridyl | CF₂Cl | H | H | 0 |
| 1.224 | H | CF₂Cl | H | H | 1 |
| 1.225 | Cl | CF₂Cl | H | H | 1 |
| 1.226 | CHF₂ | CF₂Cl | H | H | 1 |
| 1.227 | CCl₃ | CF₂Cl | H | H | 1 |
| 1.228 | CClF₂ | CF₂Cl | H | H | 1 |
| 1.229 | CF₃ | CF₂Cl | H | H | 1 |
| 1.23 | CH₃ | CF₂Cl | H | H | 1 |
| 1.231 | CH₂CH₃ | CF₂Cl | H | H | 1 |
| 1.232 | CH(CH₃)₂ | CF₂Cl | H | H | 1 |
| 1.233 | (CH₂)₂CH₃ | CF₂Cl | H | H | 1 |
| 1.234 | C(CH₃)₃ | CF₂Cl | H | H | 1 |
| 1.235 | CH₂F | CF₂Cl | H | H | 1 |
| 1.236 | CH₂Cl | CF₂Cl | H | H | 1 |
| 1.237 | CH₂OH | CF₂Cl | H | H | 1 |
| 1.238 | CH₂OCOCH₃ | CF₂Cl | H | H | 1 |
| 1.239 | CH₂OCOPh | CF₂Cl | H | H | 1 |
| 1.24 | CH₂OCH₃ | CF₂Cl | H | H | 1 |
| 1.241 | CH₂OCH₂CH₃ | CF₂Cl | H | H | 1 |
| 1.242 | CH₂SMe | CF₂Cl | H | H | 1 |
| 1.243 | CH₂SOMe | CF₂Cl | H | H | 1 |
| 1.244 | CH₂SO₂Me | CF₂Cl | H | H | 1 |
| 1.245 | CH₂SO₂Ph | CF₂Cl | H | H | 1 |
| 1.246 | N(CH₃)₂ | CF₂Cl | H | H | 1 |
| 1.247 | CH=CH₂ | CF₂Cl | H | H | 1 |
| 1.248 | CH₂CH=CH₂ | CF₂Cl | H | H | 1 |
| 1.249 | SO₂N(CH₃)₂ | CF₂Cl | H | H | 1 |
| 1.25 | CCH | CF₂Cl | H | H | 1 |
| 1.251 | Cyclopropyl | CF₂Cl | H | H | 1 |
| 1.252 | OPh | CF₂Cl | H | H | 1 |
| 1.253 | OCH₃ | CF₂Cl | H | H | 1 |
| 1.254 | CO₂Me | CF₂Cl | H | H | 1 |
| 1.255 | OCH₂CCH | CF₂Cl | H | H | 1 |
| 1.256 | H | CCl₃ | H | H | 0 |
| 1.257 | Cl | CCl₃ | H | H | 0 |
| 1.258 | CH₃ | CCl₃ | H | H | 0 |
| 1.259 | CH₂CH₃ | CCl₃ | H | H | 0 |
| 1.26 | CH(CH₃)₂ | CCl₃ | H | H | 0 |
| 1.261 | (CH₂)₂CH₃ | CCl₃ | H | H | 0 |
| 1.262 | CH₂F | CCl₃ | H | H | 0 |
| 1.263 | CH₂Cl | CCl₃ | H | H | 0 |
| 1.264 | CH₂OH | CCL₃ | H | H | 0 |
| 1.265 | CH₂OCOCH₃ | CCl₃ | H | H | 0 |
| 1.266 | CH₂OCOPh | CCl₃ | H | H | 0 |
| 1.267 | CH₂OCH₃ | CCl₃ | H | H | 0 |
| 1.268 | CH₂OCH₂CH₃ | CCl₃ | H | H | 0 |

TABLE 1-continued

Compounds of formula Ie (Ie)

| Comp. No. | Ra2 | Ra5 | Ra4 | Ra3 | p |
|---|---|---|---|---|---|
| 1.269 | CH$_2$SMe | CCl$_3$ | H | H | 0 |
| 1.27 | CH$_2$SOMe | CCl$_3$ | H | H | 0 |
| 1.271 | CH$_2$SO$_2$Me | CCl$_3$ | H | H | 0 |
| 1.272 | CH$_2$SO$_2$Ph | CCl$_3$ | H | H | 0 |
| 1.273 | Cyclopropyl | CCl$_3$ | H | H | 0 |
| 1.274 | OPh | CCl$_3$ | H | H | 0 |
| 1.275 | OCH$_3$ | CCl$_3$ | H | H | 0 |
| 1.276 | CO$_2$Me | CCl$_3$ | H | H | 0 |
| 1.277 | OCH$_2$CCH | CCl$_3$ | H | H | 0 |
| 1.278 | H | CCl$_3$ | H | H | 1 |
| 1.279 | Cl | CCl$_3$ | H | H | 1 |
| 1.28 | CH$_3$ | CCl$_3$ | H | H | 1 |
| 1.281 | CH$_2$CH$_3$ | CCl$_3$ | H | H | 1 |
| 1.282 | CH(CH$_3$)$_2$ | CCl$_3$ | H | H | 1 |
| 1.283 | (CH$_2$)$_2$CH$_3$ | CCl$_3$ | H | H | 1 |
| 1.284 | CH$_2$F | CCl$_3$ | H | H | 1 |
| 1.285 | CH$_2$Cl | CCl$_3$ | H | H | 1 |
| 1.286 | CH$_2$OH | CCl$_3$ | H | H | 1 |
| 1.287 | CH$_2$OCOCH$_3$ | CCl$_3$ | H | H | 1 |
| 1.288 | CH$_2$OCOPh | CCl$_3$ | H | H | 1 |
| 1.289 | CH$_2$OCH$_3$ | CCl$_3$ | H | H | 1 |
| 1.29 | CH$_2$OCH$_2$CH$_3$ | CCl$_3$ | H | H | 1 |
| 1.291 | CH$_2$SMe | CCl$_3$ | H | H | 1 |
| 1.292 | CH$_2$SOMe | CCl$_3$ | H | H | 1 |
| 1.293 | CH$_2$SO$_2$Me | CCl$_3$ | H | H | 1 |
| 1.294 | CH$_2$SO$_2$Ph | CCl$_3$ | H | H | 1 |
| 1.295 | Cyclopropyl | CCl$_3$ | H | H | 1 |
| 1.296 | OPh | CCl$_3$ | H | H | 1 |
| 1.297 | OCH$_3$ | CCl$_3$ | H | H | 1 |
| 1.298 | CO$_2$Me | CCl$_3$ | H | H | 1 |
| 1.299 | OCH$_2$CCH | CCl$_3$ | H | H | 1 |
| 1.3 | CF$_3$ | CHF$_2$ | H | H | 0 |
| 1.301 | CH$_3$ | CHF$_2$ | H | H | 0 |
| 1.302 | CH$_2$OCH$_3$ | CHF$_2$ | H | H | 0 |
| 1.303 | CH$_2$Cl | CHF$_2$ | H | H | 0 |
| 1.304 | CH$_2$F | CHF$_2$ | H | H | 0 |
| 1.305 | CF$_3$ | CHF$_2$ | H | H | 1 |
| 1.306 | CH$_3$ | CHF$_2$ | H | H | 1 |
| 1.307 | CH$_2$OCH3 | CHF$_2$ | H | H | 1 |
| 1.308 | CH$_2$Cl | CHF$_2$ | H | H | 1 |
| 1.309 | CH$_2$F | CHF$_2$ | H | H | 1 |
| 1.31 | CH$_3$ | CF$_3$ | H | CH$_3$ | 0 |
| 1.311 | CH$_3$ | CF$_3$ | H | CH$_3$ | 1 |
| 1.312 | Cl | CF$_3$ | H | CH$_3$ | 1 |
| 1.313 | CH$_3$ | CF$_3$ | CH$_3$ | H | 0 |
| 1.314 | CH$_3$ | CF$_3$ | Ph | H | 0 |
| 1.315 | CH$_3$ | CF$_3$ | Cl | H | 0 |
| 1.316 | CH$_3$ | CF$_3$ | CO$_2$CH$_2$CH$_3$ | H | 0 |
| 1.317 | CH$_3$ | CF$_3$ | CO$_2$CH$_2$Ph | H | 0 |
| 1.318 | CH$_3$ | CF$_3$ | CH$_3$ | H | 1 |
| 1.319 | CH$_3$ | CF$_3$ | Ph | H | 1 |
| 1.32 | CH$_3$ | CF$_3$ | Cl | H | 1 |
| 1.321 | CH$_3$ | CF$_3$ | CO$_2$CH$_2$CH$_3$ | H | 1 |
| 1.322 | CH$_3$ | CF$_3$ | CO$_2$CH$_2$Ph | H | 1 |
| 1.323 | OCH$_3$ | CF$_3$ | CH$_3$ | H | 0 |
| 1.324 | CH$_2$OCH$_3$ | CF$_3$ | CH$_3$ | H | 0 |
| 1.325 | CH$_2$OCH$_3$ | CF$_3$ | Ph | H | 0 |
| 1.326 | CH$_2$OCH$_3$ | CF$_3$ | Cl | H | 0 |
| 1.327 | CH$_2$OCH$_3$ | CF$_3$ | CO$_2$CH$_2$CH$_3$ | H | 0 |
| 1.328 | CH$_2$OCH$_3$ | CF$_3$ | CO$_2$CH$_2$Ph | H | 0 |
| 1.329 | CH$_2$OCH$_3$ | CF$_3$ | CH$_3$ | H | 1 |
| 1.33 | CH$_2$OCH$_3$ | CF$_3$ | Ph | H | 1 |
| 1.331 | CH$_2$OCH$_3$ | CF$_3$ | Cl | H | 1 |
| 1.332 | CH$_2$OCH$_3$ | CF$_3$ | CO$_2$CH$_2$CH$_3$ | H | 1 |
| 1.333 | CH$_2$OCH$_3$ | CF$_3$ | CO$_2$CH$_2$Ph | H | 1 |
| 1.334 | COOCH$_3$ | H | H | H | 0 |
| 1.335 | CF$_3$ | SCH$_3$ | H | H | 0 |
| 1.336 | CH$_3$ | SCH$_3$ | H | H | 0 |
| 1.337 | CF$_3$ | SOCH$_3$ | H | H | 0 |
| 1.338 | CH$_3$ | SOCH$_3$ | H | H | 0 |
| 1.339 | CF$_3$ | SO$_2$CH$_3$ | H | H | 0 |
| 1.34 | CH$_3$ | SO$_2$CH$_3$ | H | H | 0 |
| 1.341 | CF$_3$ | SCH$_2$CH$_3$ | H | H | 0 |
| 1.342 | CH$_3$ | SCH$_2$CH$_3$ | H | H | 0 |
| 1.343 | CF$_3$ | SOCH$_2$CH$_3$ | H | H | 0 |
| 1.344 | CH$_3$ | SOCH$_2$CH$_3$ | H | H | 0 |
| 1.345 | CF$_3$ | SO$_2$CH$_2$CH$_3$ | H | H | 0 |
| 1.346 | CH$_3$ | SO$_2$CH$_2$CH$_3$ | H | H | 0 |
| 1.347 | CF$_3$ | OCH$_3$ | H | H | 0 |
| 1.348 | CH$_3$ | OCH$_3$ | H | H | 0 |
| 1.349 | CF$_3$ | OCH$_2$CF$_3$ | H | H | 0 |
| 1.35 | CH$_3$ | OCH$_2$CF$_3$ | H | H | 0 |
| 1.351 | CF$_3$ | OCH$_2$CCH | H | H | 0 |
| 1.352 | CH$_3$ | OCH$_2$CCH | H | H | 0 |
| 1.353 | CF$_3$ | CN | H | H | 0 |
| 1.354 | CH$_3$ | CN | H | H | 0 |
| 1.355 | CF$_3$ | Cl | H | H | 0 |
| 1.356 | CF$_3$ | Cl | H | H | 0 |
| 1.357 | CH$_3$ | Cl | H | H | 0 |
| 1.358 | H | Cl | H | H | 0 |
| 1.359 | CF$_3$ | OCH$_3$ | H | H | 0 |
| 1.36 | CH$_3$ | OCH$_3$ | H | H | 0 |
| 1.361 | CF$_3$ | CH$_3$ | H | CH$_3$ | 0 |
| 1.362 | H | CF$_3$ | H | CH$_3$ | 0 |
| 1.363 | H | CF$_3$ | H | CF$_3$ | 0 |
| 1.364 | H | CF$_3$ | H | CH$_2$CH$_3$ | 0 |
| 1.365 | H | CF$_3$ | H | CF$_3$ | 0 |
| 1.366 | H | CF$_3$ | H | SCH$_3$ | 0 |
| 1.367 | H | CF$_3$ | H | SOCH$_3$ | 0 |
| 1.368 | H | CF$_3$ | H | SO$_2$CH$_3$ | 0 |
| 1.369 | H | CF$_3$ | H | Cl | 0 |
| 1.37 | H | CF$_3$ | H | OCH$_3$ | 0 |
| 1.371 | H | CH$_3$ | H | CF$_3$ | 0 |
| 1.372 | H | Cl | H | CF$_3$ | 0 |
| 1.373 | H | OCH$_3$ | H | CF$_3$ | 0 |
| 1.374 | H | SCH$_3$ | H | CF$_3$ | 0 |
| 1.375 | H | SOCH$_3$ | H | CF$_3$ | 0 |
| 1.376 | CF$_2$H | SOCH$_2$CH$_3$ | H | H | 0 |
| 1.377 | CF$_2$Cl | SOCH$_2$CH$_3$ | H | H | 0 |
| 1.378 | CF$_2$H | SO$_2$CH$_2$CH$_3$ | H | H | 0 |
| 1.379 | CF$_2$Cl | SO$_2$CH$_2$CH$_3$ | H | H | 0 |
| 1.38 | CF$_2$H | OCH$_3$ | H | H | 0 |
| 1.381 | CF$_2$Cl | OCH$_3$ | H | H | 0 |
| 1.382 | CF$_2$H | OCH$_2$CF$_3$ | H | H | 0 |
| 1.383 | CF$_2$Cl | OCH$_2$CF$_3$ | H | H | 0 |
| 1.384 | CF$_2$H | OCH$_2$CCH | H | H | 0 |
| 1.385 | CF$_2$Cl | OCH$_2$CCH | H | H | 0 |
| 1.386 | CF$_2$H | CN | H | H | 0 |
| 1.387 | CF$_2$Cl | CN | H | H | 0 |
| 1.388 | CF$_2$H | Cl | H | H | 0 |
| 1.389 | CF$_2$Cl | Cl | H | H | 0 |
| 1.39 | CF$_2$H | OCH$_3$ | H | H | 0 |
| 1.391 | CF$_2$Cl | OCH$_3$ | H | H | 0 |
| 1.392 | CF$_3$ | CH$_2$OCH$_3$ | H | H | 0 |
| 1.393 | CF$_3$ | CH$_2$OCH$_3$ | H | H | 1 |
| 1.394 | CF$_2$Cl | CH$_2$OCH$_3$ | H | H | 0 |

TABLE 1-continued
Compounds of formula Ie
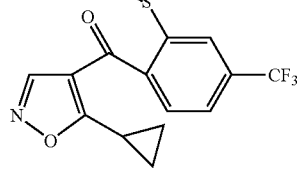
(Ie)
| Comp. No. | Ra₂ | Ra₅ | Ra₄ | Ra₃ | p |
|---|---|---|---|---|---|
| 1.395 | CF₂Cl | CH₂OCH₃ | H | H | 1 |
| 1.396 | CF$_{2H}$ | CH₂OCH₃ | H | H | 0 |
| 1.397 | CF$_{2H}$ | CH₂OCH₃ | H | H | 1 |
| 1.398 | CN | CF₃ | H | H | 0 |
TABLE 2
Preferred HPPD inhibitors according to the present invention:
| Comp. No. | Structure: |
|---|---|
| 2.01 | 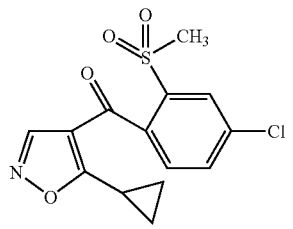 |
| 2.02 | |
| 2.03 | |
| 2.04 | |
| 2.05 | 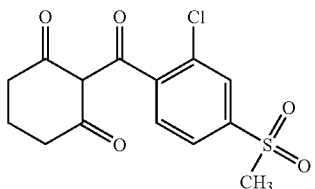 |
| 2.06 | |
| 2.07 | |
| 2.08 | 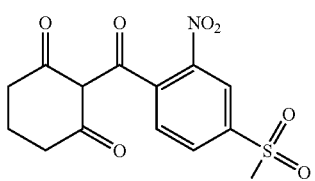 |

TABLE 2-continued

Preferred HPPD inhibitors accordincg to the present invention:

| Comp. No. | Structure: |
|---|---|
| 2.09 | |
| 2.10 | |
| 2.11 | |
| 2.12 | |
| 2.13 | |
| 2.14 | |
| 2.15 | |
| 2.16 | |
| 2.17 | |
| 2.18 | |
| 2.19 | |

The compounds 2.04, 2.10 and 2.13 are especially preferred. Compound No. 2.01 is known from The Pesticide Manual 12$^{th}$ ed., Entry No.: 467. Compound No. 2.02 (4-chloro-2-mesylphenyl-5-cyclopropyl-1,2-oxazol-4-yl ketone) is registered under Chemical Abstracts No. 141112-06-3. Compound No. 2.03 is known from The Pesticide Manual 12$^{th}$ ed., Entry No.: 710, and compound No. 2.04 is described under Entry No. 500. Compound No. 2.05 is known from The Pesticide Manual 12$^{th}$ ed., under Entry No.: 71; compound No. 2.06 under Entry No. 663; compound No. 2.07 under Entry No. 666; and compound No. 2.08 under Entry No. 70. Compounds No. 2.09 and 2.10 are described in WO 98/31681, and mixtures of those compounds with herbicides are known from WO 99/65314. Compound No. 2.11 is described in Chemical Abstracts under the registration number CAS 192708-91-1.

Compound No. 2.12 is described in WO 98/42677 A1 and U.S. Pat. No. 6,211,403 B1 and has the Chemical Abstracts registration number 128133-27-7. Compounds No. 2.13 and 2.14 and their preparation are known from WO/0015615. Compound 2.15 is described in EP-A-0 496 631, and compound 2.16 is described in WO 03/092380. Compound No. 2.17 is known from WO 02/085118, and compound No. 2.18 from WO 02/021924. Compound No. 2.19 is described in WO 04/021788.

What is claimed is:

1. A method of labelling soya varieties as to their suitability as a subsequent crop to maize when weed control in that maize crop has been carried out using HPPD inhibitor herbicides, wherein:
 a) in a first step, a reference soya variety is selected which, when grown as a subsequent crop to maize wherein weed control has been carried out using HPPD inhibitor herbicides and wherein soil residues of the HPPD inhibitor herbicides exist at the time the soya variety is subsequently grown, exhibits from 5 to 20% phytotoxicity with respect to those HPPD inhibitor herbicide soil residues;
 b) in a second step, the phytotoxicity of soya varieties when grown in the same manner as the reference variety in the first step is determined in relation to that reference soya variety in the form of a factor; and
 c) in a third step, said soya varieties are labelled with said factor.

2. A method according to claim 1, wherein the reference soya variety is a variety selected from NK S40-R9, Pioneer 94B01, NK S46-W8, Mustang M-222RR, AGI 7370 RR, Pioneer 9492, Pioneer 93B67, Pioneer 90B51, S. Grow SG948R and Pioneer 94B54.

3. A method according to claim 1, wherein the HPPD inhibitor herbicide is a compound of formula Ie

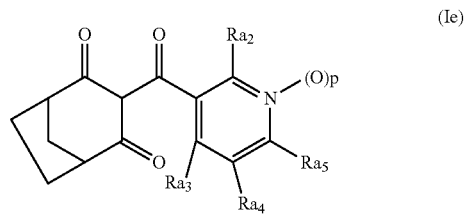

wherein p is 0 or 1; $Ra_2$ is $C_1$-$C_4$alkoxy-$C_1$-$C_4$alkoxy-$C_1$-$C_4$alkyl; $Ra_3$ and $Ra_4$ are hydrogen; and $Ra_5$ is $C_1$-$C_3$haloalkyl.

* * * * *